United States Patent
Ben-Ami et al.

(10) Patent No.: US 12,223,771 B2
(45) Date of Patent: *Feb. 11, 2025

(54) DETERMINING DIGITAL MARKERS INDICATIVE OF A NEUROLOGICAL CONDITION

(71) Applicant: NeuraLight Ltd., Tel Aviv (IL)

(72) Inventors: Edmund Ben-Ami, Tel Aviv (IL); Micha Yochanan Breakstone, Austin, TX (US); Rotem Zvi Bar-Or, Jerusalem (IL); Vladimir Anisimov, Tel-Aviv (IL)

(73) Assignee: NeuraLight, Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/734,323

(22) Filed: Jun. 5, 2024

(65) Prior Publication Data

US 2024/0321007 A1    Sep. 26, 2024

Related U.S. Application Data

(63) Continuation of application No. 18/485,031, filed on Oct. 11, 2023, now Pat. No. 12,033,432, which is a (Continued)

(51) Int. Cl.
*G06V 40/18* (2022.01)
*A61B 3/00* (2006.01)
(Continued)

(52) U.S. Cl.
CPC ............ *G06V 40/18* (2022.01); *A61B 3/0025* (2013.01); *A61B 3/113* (2013.01); *G06F 3/013* (2013.01);
(Continued)

(58) Field of Classification Search
CPC ...... G06V 40/18; G06V 10/82; G06T 7/0012; G06T 2207/20081; G06T 2207/30041;
(Continued)

(56) References Cited

U.S. PATENT DOCUMENTS

| | | |
|---|---|---|
| 6,820,979 B1 | 11/2004 | Stark et al. |
| 7,428,320 B2 | 9/2008 | Northcott et al. |

(Continued)

FOREIGN PATENT DOCUMENTS

| | | |
|---|---|---|
| CA | 2618352 A1 | 2/2007 |
| CN | 106265006 A | 1/2017 |

(Continued)

OTHER PUBLICATIONS

Qidwai et al. "Blind Deconvolution for Retinal Image Enhancement." IEEE EMBS Conference on Biomedical Engineering and Sciences (IECBES), Nov. 30, 2010, DOI: 10.1109/IECBES.2010. 5742192, pp. 20-25 (Year: 2010).*

(Continued)

*Primary Examiner* — Jon Chang
(74) *Attorney, Agent, or Firm* — Sterne, Kessler, Goldstein & Fox P.L.L.C.

(57) ABSTRACT

Disclosed are system, method, and computer program product embodiments for determining a digital marker indicative of a neurological condition. An embodiment operates by detecting a region of interest in an image frame of a face of a user. The region of interest includes an eye of the user and the image frame is obtained from a video stream. The embodiment then generates a point spread function (PSF) based on acquired data and a portion of the image frame specified by the region of interest, performs deconvolution on the portion of the image frame specified by the region of interest using the PSF, determines a set of oculometric parameters of the eye of the user using the deconvolved (Continued)

image, and determines one or more digital markers of the user based on the set of oculometric parameters. The one or more digital markers are indicative of a neurological condition of the user.

20 Claims, 11 Drawing Sheets

Related U.S. Application Data continuation-in-part of application No. 17/722,095, filed on Apr. 15, 2022, and a continuation-in-part of application No. 17/734,896, filed on May 2, 2022.

(60) Provisional application No. 63/183,388, filed on May 3, 2021.

(51) Int. Cl.
  *A61B 3/113* (2006.01)
  *G06F 3/01* (2006.01)
  *G06T 7/00* (2017.01)

(52) U.S. Cl.
  CPC .. *G06T 7/0012* (2013.01); *G06T 2207/20081* (2013.01); *G06T 2207/30041* (2013.01)

(58) Field of Classification Search
  CPC . G06T 2207/10016; G06T 2207/20084; G06T 7/0016; G06T 7/246; A61B 3/0025; A61B 3/113; G06F 3/013; G06N 3/04; G06N 3/084; G06N 3/09
  See application file for complete search history.

(56) References Cited

U.S. PATENT DOCUMENTS

| | | | |
|---|---|---|---|
| 7,753,525 B2 | 7/2010 | Hara et al. | |
| 7,869,627 B2 | 1/2011 | Northcott et al. | |
| 8,061,840 B2 | 11/2011 | Mizuochi | |
| 8,132,916 B2 | 3/2012 | Johansson | |
| 9,965,860 B2 | 5/2018 | Nguyen et al. | |
| 10,016,130 B2 | 7/2018 | Ganesan et al. | |
| 10,109,056 B2 | 10/2018 | Nguyen et al. | |
| 10,231,614 B2 | 3/2019 | Krueger | |
| 10,575,728 B2 | 3/2020 | Zakariaie et al. | |
| 10,713,813 B2 | 7/2020 | De Villers-Sidani et al. | |
| 10,713,814 B2 | 7/2020 | De Villers-Sidani et al. | |
| 11,074,714 B2 | 7/2021 | De Villers-Sidani et al. | |
| 11,382,545 B2 | 7/2022 | Zakariaie et al. | |
| 11,503,998 B1 | 11/2022 | De Villers-Sidani et al. | |
| 11,513,593 B2 | 11/2022 | Drozdov et al. | |
| 11,514,720 B2 | 11/2022 | Haimovitch-Yogev et al. | |
| 11,776,315 B2 | 10/2023 | Haimovitch-Yogev et al. | |
| 12,033,432 B2* | 7/2024 | Ben-Ami ................. G06N 3/04 |
| 2005/0228236 A1 | 10/2005 | Diederich et al. | |
| 2007/0009169 A1 | 1/2007 | Bhattacharjya | |
| 2009/0018419 A1 | 1/2009 | Torch | |
| 2014/0171756 A1 | 6/2014 | Waldorf et al. | |
| 2014/0320397 A1 | 10/2014 | Hennessey et al. | |
| 2014/0364761 A1 | 12/2014 | Benson et al. | |
| 2015/0077543 A1 | 3/2015 | Kerr et al. | |
| 2015/0293588 A1 | 10/2015 | Strupczewski et al. | |
| 2016/0150955 A1 | 6/2016 | Kiderman et al. | |
| 2017/0135577 A1 | 5/2017 | Komogortsev | |
| 2017/0151089 A1 | 6/2017 | Chernyak | |
| 2017/0231490 A1 | 8/2017 | Toth et al. | |
| 2017/0249434 A1 | 8/2017 | Brunner | |
| 2018/0018515 A1 | 1/2018 | Spizhevoy et al. | |
| 2019/0246969 A1* | 8/2019 | Thomas ................ A61B 3/0025 |
| 2020/0268296 A1 | 8/2020 | Alcaide et al. | |
| 2020/0305708 A1 | 10/2020 | Krueger | |
| 2020/0323480 A1 | 10/2020 | Shaked et al. | |
| 2020/0405148 A1 | 12/2020 | Tran | |
| 2021/0174959 A1 | 6/2021 | Abel Fernandez | |
| 2021/0186318 A1 | 6/2021 | Yellin et al. | |
| 2021/0186395 A1 | 6/2021 | Zakariaie et al. | |
| 2021/0186397 A1 | 6/2021 | Weisberg et al. | |
| 2021/0228142 A1* | 7/2021 | Sheehy ................ A61B 5/1103 |
| 2021/0248720 A1* | 8/2021 | Ziesche ................ A61B 90/20 |
| 2021/0327595 A1 | 10/2021 | Abdallah | |
| 2022/0019791 A1 | 1/2022 | Drozdov et al. | |
| 2022/0206571 A1 | 6/2022 | Drozdov et al. | |
| 2022/0211310 A1 | 7/2022 | Zakariaie et al. | |
| 2022/0236797 A1 | 7/2022 | Drozdov et al. | |
| 2022/0301294 A1 | 9/2022 | Boutinon | |
| 2022/0313083 A1 | 10/2022 | Zakariaie et al. | |
| 2022/0351545 A1 | 11/2022 | Ben-Ami et al. | |
| 2022/0354363 A1 | 11/2022 | Ben-Ami et al. | |
| 2022/0390771 A1 | 12/2022 | David et al. | |
| 2023/0074569 A1 | 3/2023 | Drozdov et al. | |
| 2023/0233072 A1 | 7/2023 | Haimovitch-Yogev et al. | |
| 2023/0334326 A1 | 10/2023 | Haimovitch-Yogev et al. | |
| 2024/0037987 A1 | 2/2024 | Ben-Ami et al. | |
| 2024/0119594 A1 | 4/2024 | Ben-Ami et al. | |

FOREIGN PATENT DOCUMENTS

| | | |
|---|---|---|
| EP | 1947604 A1 | 7/2008 |
| WO | WO-2020235939 A2 | 11/2020 |
| WO | WO-2021097300 A1 | 5/2021 |

OTHER PUBLICATIONS

Torres-Salomao et al. "Pupil Diameter Size Marker for Incremental Mental Stress Detection." 17th International Conference on E-health Networking, Application & Services (HealthCom), DOI: 10.1109/HealthCom.2015.7454513, Oct. 14, 2015, pp. 286-291 (Year: 2015).*
Akinyelu, A.A. and Blignaut, P., "Convolutional Neural Network-Based Technique for Gaze Estimation on Mobile Devices," Frontiers in Artificial Intelligence 4:796825 11 pages, Frontiers Media SA, Switzerland (Jan. 2022).
Ali, E.N., et al., "Pupillary Response to Sparse Multifocal Stimuli in Multiple Sclerosis Patients," Multiple Sclerosis Journal 20(7):854-861, SAGE Publications, United Kingdom (Nov. 2013).
Aljaafreh, A., et al., "A Low-cost Webcam-based Eye Tracker and Saccade Measurement System," International Journal of Circuits, Systems and Signal Processing 14:102-107, (Apr. 2020).
Alnajar, F., et al., "Auto-Calibrated Gaze Estimation Using Human Gaze Patterns," International Journal of Computer Vision 124:223-236, (2017).
Bafna, T., et al., "EyeTell: Tablet-based Calibration-free Eye-typing Using Smooth-pursuit Movements," Proceedings of the ETRA '21 Short Papers, (2021).
Bedell, H.E., et al., "Eye Movement Testing in Clinical Examination," Vision Research 90:32-37, Elsevier Science Limited, United Kingdom (Sep. 2013).
Bijvank, J.A.N., et al., "Quantification of Visual Fixation in Multiple Sclerosis," Investigative Ophthalmology & Visual Science 60(5):1372-1383, Association for Research In Vision and Ophthalmology (Arvo), United States (Apr. 2019).
Borza, D., et al., "Real-Time Detection and Measurement of Eye Features from Color Images," Sensors 16(7):1105 1-24, MDPI, Switzerland (Jul. 2016).
Chen, S. and Epps, J., "Eyelid and Pupil Landmark Detection and Blink Estimation Based on Deformable Shape Models for Near-Field Infrared Video," Frontiers in ICT 6:18 1-11, (Oct. 2019).
Cherng, Y., et al., "Background Luminance Effects on Pupil Size Associated With Emotion and Saccade Preparation," Scientific Reports 10(1):15718 11 Pages, Nature Publishing Group, United Kingdom (Sep. 2020).
Chernov, N., et al., "Fitting Quadratic Curves to Data Points," British Journal of Mathematics & Computer Science 4(1):33-60, (2014).
De Almeida Junior, F.L., et al., "Image Quality Treatment to Improve Iris Biometric Systems," Infocomp Journal of Computer Science 16(1-2):21-30, (2017).

(56) References Cited

OTHER PUBLICATIONS

De Seze, J., et al., "Pupillary Disturbances in Multiple Sclerosis: Correlation With MRI Findings," Journal of the Neurological Sciences 188(1-2):37-41, Elsevier, Netherlands (Jul. 2001).
De Villers-Sidani, E., et al., "A Novel Tablet-based Software for the Acquisition and Analysis of Gaze and Eye Movement Parameters: A Preliminary Validation Study in Parkinson's Disease," Frontiers in Neurology 14(1204733):1-10 , Frontiers Research Foundation, Switzerland (Jun. 2023).
De Villers-Sidani, E., et al., "Oculomotor Analysis to Assess Brain Health: Preliminary Findings From a Longitudinal Study of Multiple Sclerosis Using Novel Tablet-based Eye-tracking Software," Frontiers in Neurology 14(1243594):1-11, Frontiers Research Foundation, Switzerland (Sep. 2023).
Derwenskus, J., et al., "Abnormal Eye Movements Predict Disability in MS: Two-year Follow-up," Annals of the New York Academy of Sciences 1039:521-523, Blackwell, United States (Apr. 2005).
Felmingham, K., "Eye Tracking and PTSD," Comprehensive Guide to Post-traumatic Stress Disorder Chapter 69:1241-1256, (Jan. 2015).
Ferreira, M., et al., "Using Endogenous Saccades to Characterize Fatigue in Multiple Sclerosis," Multiple Sclerosis and Related Disorders 14:16-22, Elsevier B. V., Netherlands (May 2017).
Fielding, J., et al., "Ocular Motor Signatures of Cognitive Dysfunction in Multiple Sclerosis," Nature Reviews. Neurology, 11(11):637-645, Nature Publishing Group, United Kingdom (Nov. 2015).
Fink, L., et al., "From Pre-processing to Advanced Dynamic Modeling of Pupil Data," Behavior Research Methods 56(3):1376-1412, Springer, United States (Jun. 2023).
Frohman, E.M., et al., "Quantitative Oculographic Characterisation of Internuclear Ophthalmoparesis in Multiple Sclerosis: The Versional Dysconjugacy Index Z Score," Journal of Neurology, Neurosurgery, and Psychiatry 73(1):51-55, BMJ Publishing Group, United Kingdom (Jul. 2002).
Frohman, E.M., et al., "The Neuro-Ophthalmology of Multiple Sclerosis", The Lancet Neurology, 4(2):111-121, Lancet Public Group, United Kingdom (Feb. 2005).
Frohman, T.C., et al., "Accuracy of Clinical Detection of INO in MS: Corroboration With Quantitative Infrared Oculography," Neurology 61(6):848-850, Lippincott Williams & Wilkins, United States (Sep. 2003).
Grillini, A., et al., "Eye Movement Evaluation in Multiple Sclerosis and Parkinson's Disease Using a Standardized Oculomotor and Neuro-Ophthalmic Disorder Assessment (SONDA)," Frontiers in Neurology 11:971 1-15, Frontiers Research Foundation, Switzerland (Sep. 2020).
Guri, M., et al., "BRIGHTNESS: Leaking Sensitive Data from Air-Gapped Workstations via Screen Brightness," IEEE 12th CMI Conference on Cybersecurity and Privacy 7 pages, (2020).
Hasasneh, A., et al., "Deep Learning Approach for Automatic Classification of Ocular and Cardiac Artifacts in Meg Data," Hindawi Journal of Engineering, 1-10, (Apr. 2018).
Hoffner, S., et al., "Gaze Tracking Using Common Webcams," Osnabruck University, 89 pages (Feb. 2018).
Holzman, P.S., et al., "Eye-tracking Dysfunctions in Schizophrenic Patients and Their Relatives," Archives of General Psychiatry 31(2):143-151, American Medical Association, United States (Aug. 1974).
Hooge, I.T.C., et al., "Gaze Tracking Accuracy in Humans: One Eye is Sometimes Better Than Two," Behavior Research Methods 51(6):2712-2721, Springer, United States (Dec. 2019).
Hou, L., et al., "Illumination-Based Synchronization of High-Speed Vision Sensors," Sensors 10(6):5530-5547, Basel, Switzerland (2010).
Hutt, S. and D'Mello, S.K., "Evaluating Calibration-free Webcam-based Eye Tracking for Gaze-based User Modeling," ICMI '22: Proceedings of the 2022 International Conference on Multimodal Interaction 224-235, (Nov. 2022).
International Search Report and Written Opinion for Application No. PCT/US2022/027201, mailed on Sep. 19, 2022, 10 pages.
International Search Report and Written Opinion for Application No. PCT/US2022/027312, mailed on Oct. 27, 2022, 10 pages.
Jakobsen, J., "Pupillary Function in Multiple Sclerosis," Acta Neurologica Scandinavica 82(6):392-395, Wiley-Blackwell, Denmark (Dec. 1990).
Jamaludin, S., et al., "Deblurring of Noisy Iris Images in Iris Recognition," Bulletin of Electrical Engineering and Informatics (BEEI) 10(1):156-159, (Feb. 2021).
Joyce, D.S., et al., "Melanopsin-mediated Pupil Function is Impaired in Parkinson's Disease," Scientific Reports 8(1):7796, Nature Publishing Group, United Kingdom (May 2018).
Kelbsch, C., et al., "Standards in Pupillography," Frontiers in Neurology 10(129):1-26, Frontiers Research Foundation, Switzerland (Feb. 2019).
Krafka, K., et al., "Eye Tracking for Everyone," The IEEE Conference on Computer Vision and Pattern Recognition (CVPR) 2176-2184, (Jun. 2016).
Lai, H., et al., "Measuring Saccade Latency Using Smartphone Cameras," IEEE Journal of Biomedical and Health Informatics 24(3):885-897, Institute of Electrical and Electronics Engineers, United States (Mar. 2020).
Liu, G., et al., "A Differential Approach for Gaze Estimation," IEEE Transactions on Pattern Analysis and Machine Intelligence 43(3):1092-1099, IEEE Computer Society, United States (Mar. 2021).
Liu, J., et al., "Iris Image Deblurring Based on Refinement of Point Spread Function," Chinese Conference on Biometric Recognition (CCBR), Lecture Notes in Computer Science 7701:184-192, (Dec. 2012).
Lizak, N., et al., "Impairment of Smooth Pursuit as a Marker of Early Multiple Sclerosis," Frontiers in Neurology 7(3):206 1-7, Frontiers Research Foundation, Switzerland (Nov. 2016).
Mahanama, B., et al., "Eye Movement and Pupil Measures: A Review," Frontiers in Computer Science 3:733531 1-12, (Jan. 2022).
Matza, L.S., "Multiple Sclerosis Relapse: Qualitative Findings From Clinician and Patient Interviews," Multiple Sclerosis and Related Disorders 27 Pages, Elsevier B. V., Netherlands (Jan. 2019).
Model, D., "A Calibration Free Estimation of the Point of Gaze and Objective Measurement of Ocular Alignment in Adults and Infants," University of Toronto 160 pages, (2011).
Mollers, Maximilian., "Calibration-Free Gaze Tracking an Experimental Analysis," RWTH Aachen University 111 pages, (2007).
Niestroy, A., "Neuro-ophthalmologic Aspects of Multiple Sclerosis: Using Eye Movements as a Clinical and Experimental Tool," Clinical Ophthalmology 1(3):267-272, Dove Medical Press, New Zealand (Sep. 2007).
Park, S., et al., "Few-Shot Adaptive Gaze Estimation," Proceedings of the IEEE/CVF International Conference on Computer Vision (ICCV), 13 pages, (2019).
Patel, A.S., et al., "Optical Axes and Angle Kappa," American Academy of Ophthalmology, (Oct. 2021).
Peysakhovich, V., et al., "The Impact of Luminance on Tonic and Phasic Pupillary Responses to Sustained Cognitive Load," International Journal of Psychophysiology 112:40-45, Elsevier, Netherlands (Feb. 2017).
Pfeuffer, K., et al., "Pursuit Calibration: Making Gaze Calibration Less Tedious and More Flexible," UIST 13 Proceedings of the 26th Annual Acm Symposium on User Interface Software and Technology 261-270, (Oct. 2013).
Pi, J. and Shi, B.E., et al., "Task-embedded Online Eye-tracker Calibration for Improving Robustness to Head Motion," Proceedings of the 11th ACM Symposium on Eye Tracking Research & Applications ETRA '19 8:1-9, (Jun. 2019).
Polak, P.E., et al., "Locus Coeruleus Damage and Noradrenaline Reductions in Multiple Sclerosis and Experimental Autoimmune Encephalomyelitis," Brain 134(Pt 3):665-677, Oxford University Press, United Kingdom (Mar. 2011).
Rasulo, F.A., et al., "Essential Noninvasive Multimodality Neuromonitoring for the Critically III Patient," Critical Care 24(1):100 12 Pages, BioMed Central Ltd, United Kingdom (Mar. 2020).
Rayner, K., "Eye Movements in Reading and Information Processing: 20 Years of Research," Psychological Bulletin 124(3):372-422, American Psychological Association, United States (Nov. 1998).

(56) References Cited

OTHER PUBLICATIONS

Rodrigues, A.C., "Response Surface Analysis: A Tutorial for Examining Linear and Curvilinear Effects," Journal of Contemporary Administration 25(6):1-14, (Apr. 2021).
Romero, K., et al., "Neurologists' Accuracy in Predicting Cognitive Impairment in Multiple Sclerosis," Multiple Sclerosis and Related Disorders 4(4):291-295, Elsevier B. V., Netherlands (Jul. 2015).
Schuler, C.J., "Machine Learning Approaches to Image Deconvolution," Dissertation University of Tubingen, 1-142, Germany (2017).
Schweitzer, R and Rolfs, M., "An Adaptive Algorithm for Fast and Reliable Online Saccade Detection," Behavior Research Methods 52(3):1122-1139, Springer, United States (Jun. 2020).
Serra, A., et al., "Eye Movement Abnormalities in Multiple Sclerosis: Pathogenesis, Modeling, and Treatment," Frontiers in Neurology 9(31):1-7, Frontiers Research Foundation, Switzerland (Feb. 2018).
Serra, A., et al., "Role of Eye Movement Examination and Subjective Visual Vertical in Clinical Evaluation of Multiple Sclerosis," Journal of Neurology 250(5):569-575, Springer-Verlag, Germany (May 2003).
Servillo, G., et al., "Bedside Tested Ocular Motor Disorders in Multiple Sclerosis Patients," Multiple Sclerosis International 2014:732329 1-5, Hindawi Publishing Corporation, Egypt (Apr. 2014).
Sheehy, C.K., et al., "Fixational Microsaccades: A Quantitative and Objective Measure of Disability in Multiple Sclerosis," Multiple Sclerosis 26(3):343-353, SAGE Publications, United Kingdom (Mar. 2020).
Smith, J.D., "Viewpointer: Lightweight Calibration-free Eye Tracking for Ubiquitous Handsfree Deixis," UIST 05: Proceedings of the 18th Annual ACM Symposium on User Interface Software and Technology, 84 pages (2005).
Strobl, M.A.R., et al., "Look Me in the Eye: Evaluating the Accuracy of Smartphone-based Eye Tracking for Potential Application in Autism Spectrum Disorder Research," Biomedical Engineering Online 18(1):51 1-12, BioMed Central, United Kingdom (May 2019).
System and Method for Measuring Delay from Monitor Output to Camera Sensor, Unpublished Disclosure; 16 pages.
Teikari, P., et al., "Embedded Deep Learning in Ophthalmology: Making Ophthalmic Imaging Smarter," Therapeutic Advances in Ophthalmology, 1-21, Sage Publications Limited, United States (Mar. 2019).
Tur, C., et al., "Assessing Treatment Outcomes in Multiple Sclerosis Trials and in the Clinical Setting," Nature Reviews. Neurology 14(2):164 Pages, Nature Publishing Group, United Kingdom (Feb. 2018).
Valliappan, N., et al., "Accelerating Eye Movement Research via Accurate and Affordable Smartphone Eye Tracking," Nature Communications 11(1):4553 1-12, Nature Publishing Group, United Kingdom (Sep. 2020).
Valliappan, N., et al., "Accelerating Eye Movement Research via Accurate and Affordable Smartphone Eye Tracking," Nature Communications 11(1):4553 1-18, Nature Publishing Group, United Kingdom (Jul. 2020).
Van Munster, C.E.P., et al., "Outcome Measures in Clinical Trials for Multiple Sclerosis," CNS Drugs 31(3):217-236, Springer International, New Zealand (Mar. 2017).
Wang, K. and Ji, Q., "3D Gaze Estimation without Explicit Personal Calibration," Pattern Recognition 79:216-227, Elsevier, (Jul. 2018).
Williams, B.M., et al., "Fast Blur Detection and Parametric Deconvolution of Retinal Fundus Images," Fetal, Infan and Ophthalmic Medical Image Analysis, 1-8, Springer, Cham (2017).
Yang, T., et al., "Gaze Angle Estimate and Correction in Iris Recognition," IEEE Symposium on Computational Intelligence in Biometrics and Identity Management (CIBIM) 7 Pages, (Dec. 2014).
Zammarchi, G., et al., "Application of Eye Tracking Technology in Medicine: A Bibliometric Analysis," Vision 5(4):56 1-14, MDPI AG, Switzerland (Nov. 2021).
Zhang, Y., et al., "Luminance Effects on Pupil Dilation in Speech-in-noise Recognition," PLoS One 17(12):e0278506 1-18, Public Library of Science, United States (Dec. 2022).

* cited by examiner

DETERMINING DIGITAL MARKERS INDICATIVE OF A NEUROLOGICAL CONDITION

CROSS REFERENCE TO RELATED PATENT APPLICATIONS

This application is a continuation of U.S. patent application Ser. No. 18/485,031, entitled "DETERMINING DIGITAL MARKERS INDICATIVE OF A NEUROLOGICAL CONDITION," filed on Oct. 11, 2023, which is a continuation in part of U.S. patent application Ser. No. 17/722,095, entitled "OBTAINING HIGH-RESOLUTION OCULOMETRIC PARAMETERS," filed on Apr. 15, 2022, which claims the benefit of U.S. Provisional Patent Application No. 63/183,388, entitled "MEASURING HIGH RESOLUTION EYE MOVEMENTS USING BLIND DECONVOLUTION TECHNIQUES," filed on May 3, 2021, and a continuation in part of U.S. patent application Ser. No. 17/734,896, entitled "OBTAINING HIGH-RESOLUTION EYE MOVEMENT PARAMETERS," filed on May 2, 2022, which claims the benefit of U.S. Provisional Patent Application No. 63/183,388, entitled "MEASURING HIGH RESOLUTION EYE MOVEMENTS USING BLIND DECONVOLUTION TECHNIQUES," filed on May 3, 2021. The entire contents of the above referenced applications are incorporated by reference herein in their entireties.

FIELD

The present disclosure is generally directed to obtaining high-resolution oculometric parameters, and more particularly to determining a digital marker indicative of a neurological condition using the high-resolution oculometric parameters.

BACKGROUND

Progression of neurological disorders may be determined using minute eye movements. Typically, these eye movements are measured in well-controlled lab settings (e.g., no movements, controlled ambient light, or other such parameters) using dedicated devices (e.g., infrared eye trackers, pupilometers, or other such devices). However, the dedicated devices are challenging to set up, cost prohibitive, or may involve a significant amount of time and effort to create or maintain the controlled lab setup. Such challenges may discourage the continuous monitoring of the progression of neurological disorders. Continuous monitoring may help in early detection, treating, and caring for individuals that suffer from neurological disorders. Some prior technologies use neural networks to obtain these eye movements but do not attain the needed resolution for measurements (e.g., around 0.1 mm or greater resolution). Additionally, prior technologies focus on measuring reactions of the eye to specific standardized stimuli (e.g., controlled light stimulus, stimulus provided to measure specific parameters, stimulus that a patient needs to me made aware of, or other such stimulus) with controlled ambient conditions. These and other drawbacks exist.

SUMMARY

Provided herein are system, apparatus, article of manufacture, method and/or computer program product embodiments, and/or combinations and sub-combinations thereof, for efficiently determining a digital marker indicative of a neurological condition.

In some aspects, a method for efficiently determining a digital marker indicative of a neurological condition includes detecting a region of interest in an image frame of a face of a user. The region of interest includes an eye of the user and the image frame is obtained from a video stream. The method also includes generating a point spread function (PSF) based on acquired data and a portion of the image frame specified by the region of interest, performing deconvolution on the portion of the image frame specified by the region of interest using the PSF, determining a set of oculometric parameters of the eye of the user using the deconvolved image, and determining one or more digital markers of the user based on the set of oculometric parameters. The one or more digital markers are indicative of a neurological condition of the user.

In some aspects, a system for efficiently determining a digital marker indicative of a neurological condition includes one or more memories and at least one processor each coupled to at least one of the memories. The at least one processor is configured to perform operations comprising detecting a region of interest in an image frame of a face of a user. The region of interest includes an eye of the user and the image frame is obtained from a video stream. The operations further comprises generating a point spread function (PSF) based on acquired data and a portion of the image frame specified by the region of interest, performing deconvolution on the portion of the image frame specified by the region of interest using the PSF, determining a set of oculometric parameters of the eye of the user using the deconvolved image, and determining one or more digital markers of the user based on at least the set of oculometric parameters. The one or more digital markers are indicative of a neurological condition of the user.

Further features of the present disclosure, as well as the structure and operation of various embodiments, are described in detail below with reference to the accompanying drawings. It is noted that the present disclosure is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF DRAWINGS

The accompanying drawings, which are incorporated herein and form part of the specification, illustrate the present disclosure and, together with the description, further serve to explain the principles of the present disclosure and to enable a person skilled in the relevant art(s) to make and use embodiments described herein.

Figure 1A:
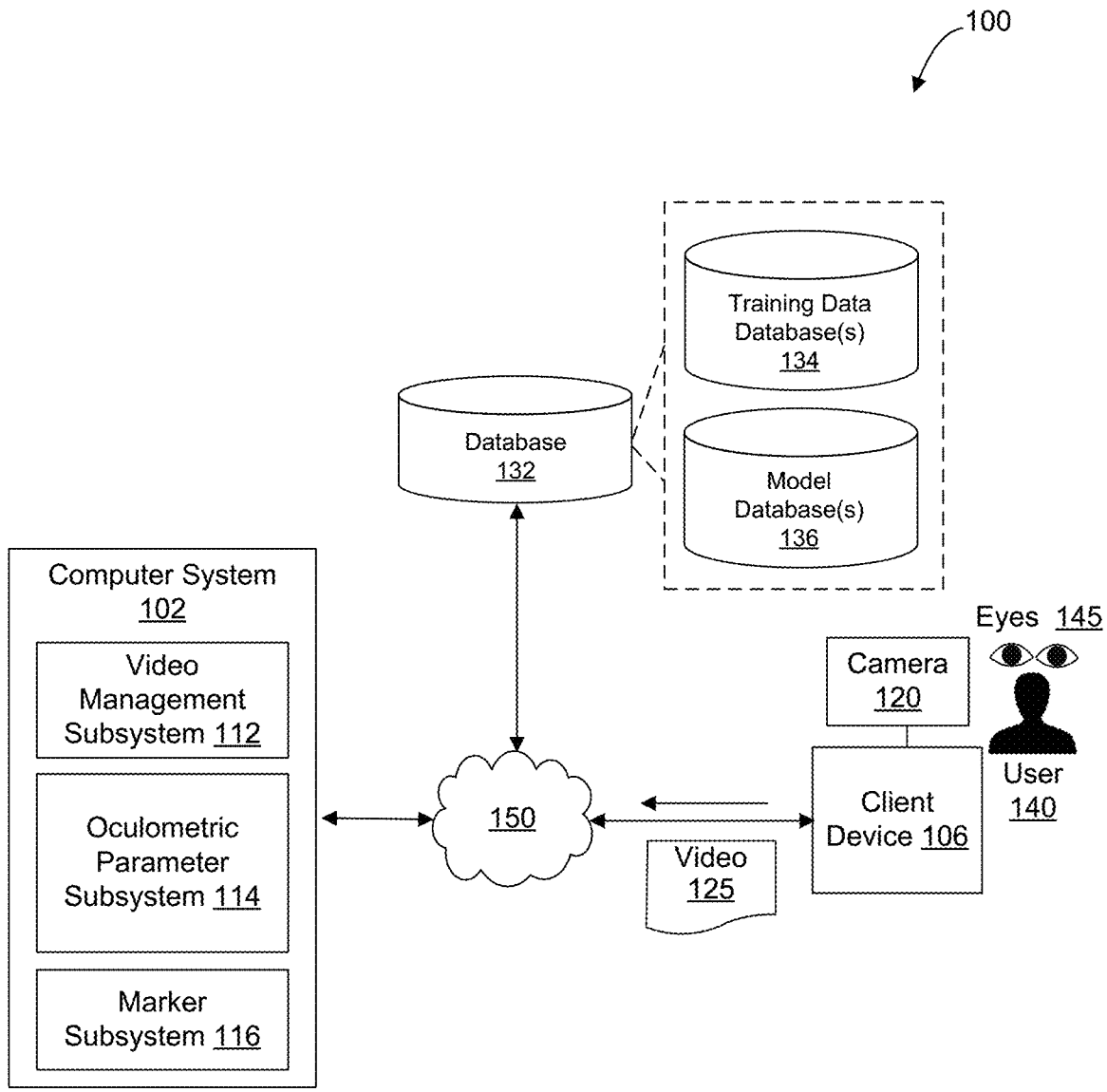
FIG. 1A shows a system for facilitating measurement of oculometric parameters and eye movements of a user, according to some embodiments.

The features of the present disclosure will become more apparent from the detailed description set forth below when takin in conjunction with the drawings, in which like reference characters identify corresponding elements throughout. In the drawings, like reference numbers generally indicate identical, functionally similar, and/or structurally similar elements. Additionally, generally, the left-most digit(s) of a reference number identifies the drawings in which the reference number first appears. Unless otherwise indicated, the drawings provided throughout the disclosure should not be interpreted as to-scale drawings.

DETAILED DESCRIPTION

This specification discloses one or more embodiments that incorporate the features of the present disclosure. The disclosed embodiment(s) are provided as examples. The scope of the present disclosure is not limited to the disclosed embodiment(s). Claimed features are defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Spatially relative terms, such as "beneath," "below," "lower," "above," "on," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The term "about," "approximately," or the like may be used herein to indicate a value of a quantity that may vary or be found to be within a range of values, based on a particular technology. Based on the particular technology, the terms may indicate a value of a given quantity that is within, for example, 1-20% of the value (e.g., ±1%, ±5%±10%, ±15%, or ±20% of the value).

Embodiments of the disclosure may be implemented in hardware, firmware, software, or any combination thereof. Embodiments of the disclosure may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, and/or instructions may be described herein as performing certain actions. However, it should be appreciated that such descriptions are merely for convenience and that such actions in fact result from computing devices, processors, controllers, or other devices executing the firmware, software, routines, instructions, etc. In the context of computer storage media, the term "non-transitory" may be used herein to describe all forms of computer readable media, with the sole exception being a transitory, propagating signal.

Aspects of the present disclosure relate to determining a digital marker indicative of a neurological condition. For example, the present disclosure relates to determining one or more digital markers based on a set of oculometric parameters determined using a deconvolved image. It improves the technological field of medical imaging and digital image processing and the functioning of computing systems that are designed to determine digital markers from images (e.g., obtained from a video stream) as described further below. The digital markers may be associated with one or more neurological conditions. The neurological conditions may include organic mental disorders (e.g., amyotrophic lateral sclerosis (ALS), multiple sclerosis (MS), and Parkinson's disease) and psychiatric disorders (e.g., post-traumatic stress disorder (PTSD), major depressive disorder (MDD), and schizophrenia).

As discussed above, monitoring the progress of neurological conditions at home provides several advantages. However, conventional equipment used to diagnostic, classify, and monitor neurological conditions in a laboratory setup are expensive and inconvenient to replicate in a home setup.

Consumer electronic devices (e.g., a laptop, a smartphone, a personal computer) may comprise a camera and are accessible for individuals. However, video streams from cameras associated with the consumer electronic devices have relatively poor point spread functions. Thus, the video streams may not be used to accurately determining the digital markers. Described herein is a process to correct for the poor point spread function. Thus, the location accuracy (e.g., eye, iris, and pupil) is improved and may be used for determining the one or more digital markers indicative of a status of mental health or neurological disorders. This can mitigate the poor image quality obtained from consumer electronic devices. Thus, the usefulness of the existing technology (e.g., medical imaging) is extended to in home-use.

The present disclosure provides an improvement in the technology of medical imaging by providing an improved process that solves the above-noted technological problems.

For example, the disclosure improves upon previous digital markers determination techniques by implementing a blind deconvolution process. The deconvolution process employs a function that is computed through an iterative process that captures data from multiple images and the consumer electronic device. The generation of the point spread function is combined with performing the deconvolution process on one or more images to determine one or more digital markers indicative of a neurological condition. In addition, the present disclosure continuously improves the accuracy of the process by providing a feedback to a prediction model for processing the video stream. In addition, the deconvolution process is iteratively applied in order to improve the accuracy of the one or more digital markers.

The present disclosure improves the functioning of a computer. For example, using the image process described herein allows the computer to use less memory because high resolution images are not acquired and stored. Instead, low resolution images may be used to determine the one or more digital markers. Thus, the disclosure provides an improvement in the functioning of the computer and an improvement in the technological fields of medical imaging and digital image processing.

Disclosed herein are method and systems to get accurate measurement of eye movement without rigidly controlling the position of the subject's eyes or the illumination of the eyes. As a result, during measurement, the position of the subject's eyes and/or the illumination of the eyes can vary without impact getting accurate measurements.

Aspects of the present disclosure capture eye measurement parameters from a video stream, determine eye movement parameters from the eye measurement parameters, and determine digital markers based on the eye movement parameters. To capture the eye measurement parameters, aspects of the present disclosure include detecting and tracking a face/eye region in one or more frames obtained from the video stream. The location of the eyelids, pupils, and irises is determined in the face/eye region. In addition, the location is refined using blind convolution.

Figure 1B:
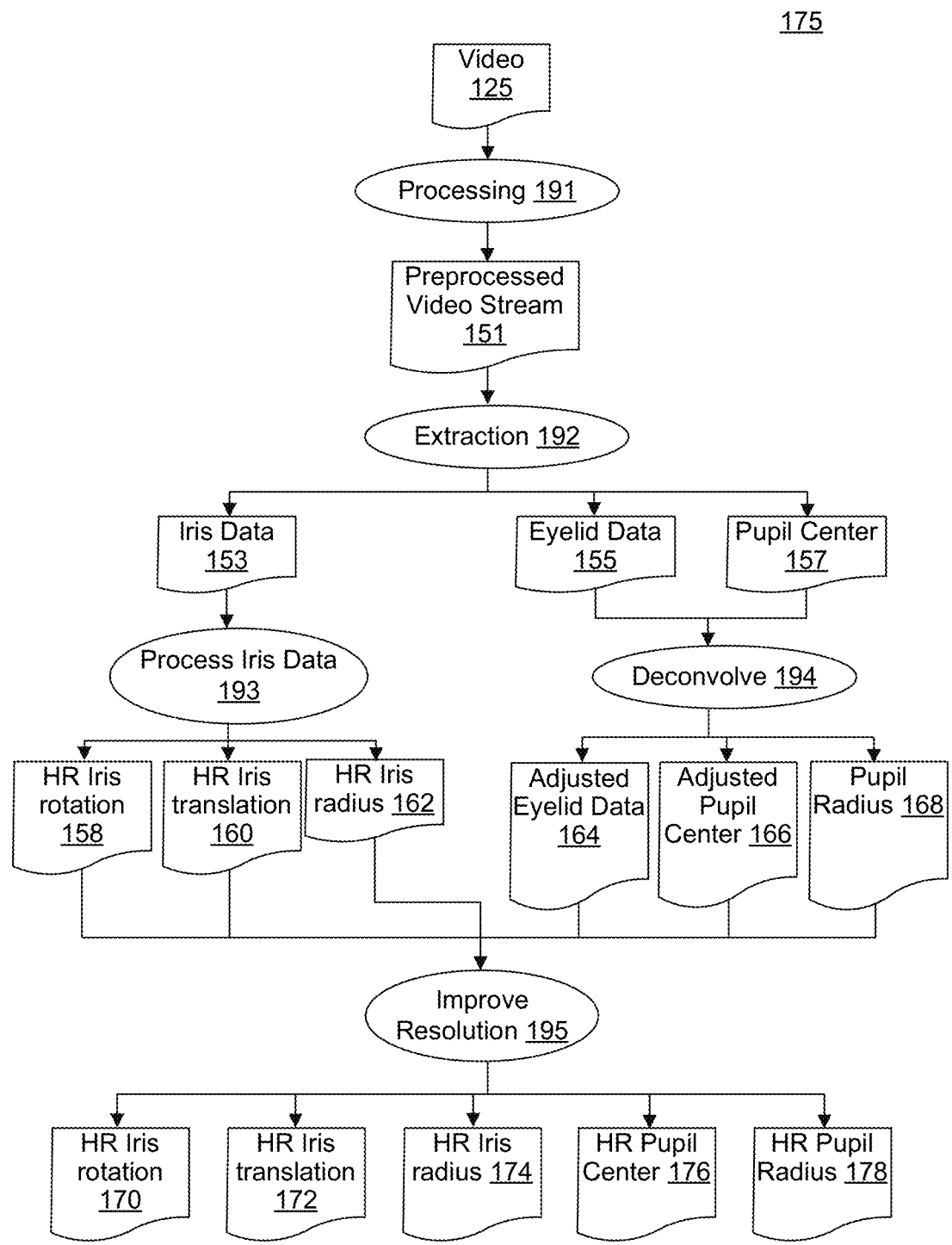
FIG. 1B shows a process of extracting high resolution (HR) oculometric parameters associated with an eye, according to some embodiments.

FIG. 1A shows a system 100 for facilitating measurement of oculometric parameters and eye movements of a user, consistent with various embodiments. FIG. 1B shows a process 175 of extracting high resolution (HR) oculometric parameters associated with an eye, consistent with various embodiments. As shown in FIG. 1A, system 100 may include computer system 102, client device 106, or other components. By the way of example, computer system 102 may include any computing device, such as a server, a personal computer (PC), a laptop computer, a tablet computer, a hand-held computer, or other computer equipment. Computer system 102 may include video management subsystem 112, oculometric parameter subsystem (OPS) 114, marker subsystem 116, or other components. The client device 106 may include any type of mobile terminal, fixed terminal, or other device. By way of example, client device 106 may include a desktop computer, a notebook computer, a tablet computer, a smartphone, a wearable device, or other client device. A user, e.g., user 140, may, for instance, utilize the client device 106 to interact with one or more servers, or other components of system 100. The camera 120 may capture still or video images of the user 140, e.g., a video of the face of the user 140. The camera 120 may be integrated with the client device 106 (e.g., smartphone camera) or may be a standalone camera (e.g., webcam or other such camera) that is connected to the client device 106.

A component of system 100 may communicate with one or more components of system 100 via a communication network 150 (e.g., Internet, a mobile phone network, a mobile voice or data network, a cable network, a public switched telephone network, or other types of communications network or combinations of communications networks). The communication network 150 may be a wireless or wired network. As an example, the client device 106 and the computer system 102 may communicate wirelessly.

It should be noted that, while one or more operations are described herein as being performed by particular components of computer system 102, those operations may, in some embodiments, be performed by other components of computer system 102 or other components of system 100. As an example, while one or more operations are described herein as being performed by components of computer system 102, those operations may, in some embodiments, be performed by components of client device 106.

It should be noted that, although some embodiments are described herein with respect to machine learning models, other prediction models (e.g., statistical models or other analytics models) may be used in lieu of or in addition to machine learning models in other embodiments (e.g., a statistical model replacing a machine learning model and a non-statistical model replacing a non-machine-learning model in one or more embodiments).

In some aspects, system 100 facilitates determination of oculometric parameters 170-178 of a user 140 at a high resolution (e.g., sub-pixel level, 0.1 mm or higher resolution) using a video stream 125 (e.g., a sequence of frames of an image of the eye) of the eye movements captured by the camera 120. The video management subsystem 112 obtains the video stream 125 from the client device 106 and stores the video stream 125 in the database 132. The OPS 114 processes the video stream 125 to extract the oculometric parameters, such as (i) pupil center 176, (ii) pupil radius 178, (iii) iris radius 174, (iv) iris translation 172, and (v) iris rotation 170 of each of the eyes, among other parameters, at a high resolution. These oculometric parameters may be used to determine eye movement parameters (e.g., pupillary response parameters and gaze parameters) that are indicative of eye movements responsive to a non-standard stimuli (e.g., a video or image displayed on the client device 106). The marker subsystem 116 may produce digital biomarkers (e.g., parameters) based on the eye movement parameters that may act as an indicator of one or more neurological disorders.

The video management subsystem 112 may store the video stream 125 in the database 132 in any of several formats (e.g., WebM, Windows Media Video, Flash Video, AVI, QuickTime, AAC, MPEG-4, or another file format). The video management subsystem 112 may also provide the video stream 125 as an input (e.g., in real-time) to the OPS 114 for generating the oculometric parameters. In some aspects, the video management subsystem 112 may perform preprocessing 191 of the video stream 125 to convert the video stream 125 to a format that is suitable for oculometric parameter extraction by the OPS 114. For example, the video management subsystem 112 may perform an extract, transform, and load (ETL) process on the video stream 125 to generate a preprocessed video stream 151 for the OPS 114. The ETL process is typically a multi-phase process where data is first extracted then transformed (e.g., cleaned, sanitized, scrubbed) and finally loaded into a target system. The data may be collated from one or more sources, and it may also be outputted to one or more destinations. In one example, the ETL process performed by the video management subsystem 112 may include adjusting color and brightness (e.g., white balance) in the video stream 125. In another example, the ETL process may include reducing noise from the video stream 125. In yet another example, the ETL process may include improving resolution of the video stream 125 based on multi-frame data, for example, by implementing one or more multi-frame super-resolution techniques that recover a high-resolution image (or a sequence) from a sequence of low-resolution images. In some aspects, super-resolution is a digital image processing technique to obtain a single high-resolution image (or a sequence) from multiple blurred low-resolution images. The basic idea of super-resolution is that the low-resolution images of the same scene contain different information because of relative subpixel shifts; thus, a high-resolution image with higher spatial information can be reconstructed by image fusion. The video management subsystem 112 may perform the above preprocessing operations and other such similar preprocessing operations to generate a preprocessed video stream 151 that is of a format suitable for the OPS 114 to perform the oculometric parameter extraction.

In some aspects, the video management subsystem 112 may obtain the preprocessed video stream 151 via a prediction model (e.g., based on the video stream 125 obtained from the client device 106). As an example, the video management subsystem 112 may input the video stream 125 obtained from the client device 106 to the prediction model, which then outputs the preprocessed video stream 151. In some aspects, the system 100 may train or configure a prediction model to facilitate the generation of a preprocessed video stream. In some aspects, system 100 may obtain a video stream from a client device associated with a user (e.g., video stream 125 having a video of a face of the user 140) and provide such information as input to a prediction model to generate predictions (e.g., preprocessed video stream 151 in which color or brightness are adjusted, resolution of the video is improved, etc.). System 100 may provide reference feedback to the prediction model and the prediction model may update one or more portions of the prediction model based on the predictions and the reference feedback. As an example, where the prediction model generates predictions based on the video stream obtained from a client device, one or more preprocessed video streams associated with such input video streams may be provided as reference feedback to the prediction model. As an example, a particular preprocessed video stream may be verified as a suitable video stream for oculometric parameter extraction by the OPS 114 (e.g., via user confirmation of the preprocessed video, via one or more subsequent actions demonstrating such goal, etc.) based on one or more user responses or one or more other user actions via one or more services. The foregoing user input information may be provided as input to the prediction model to cause the prediction model to generate predictions of the preprocessed video stream, and the verified preprocessed video stream may be provided as reference feedback to the prediction model to update the prediction model. In this way, for example, the prediction model may be trained or configured to generate more accurate predictions. In some aspects, the training dataset may include several data items in which each data item includes at least a video obtained from a client device and a corresponding preprocessed video as the ground truth.

In some aspects, the training dataset may include data obtained from an external device. The external device may include a specialized infrared (IR) eye-tracker (e.g., Tobii). The external device is used in a controlled environment. The data obtained from the external device is used to train the prediction model and to validate the accuracy of the oculometric parameters.

In some aspects, the foregoing operations for updating the prediction model may be performed with a training dataset with respect to one or more users (e.g., a training dataset associated with a given user to specifically train or configure the prediction model for the given user, a training dataset associated with a given cluster, demographic, or other group to specifically train or configure the prediction model for the given group, a training dataset associated with any given set of users, or other training dataset). As such, in some aspects, subsequent to the updating of the prediction model, system 100 may use the prediction model to facilitate generation of a preprocessed video stream for facilitating oculometric parameter extraction by the OPS 114.

The video management subsystem 112 may generate the preprocessed video stream 151 prior to inputting the video stream 125 to the OPS 114, or after storing the video stream 125 in the database 132. Further, the video management subsystem 112 may also store the preprocessed video stream 151 in the database 132 along with the video stream 125.

The OPS 114 may process the video stream 125 or the preprocessed video stream 151 to extract, determine, derive, or generate the oculometric parameters (e.g., oculometric parameters 170-178), which are characteristic of the eyes 145 of the user 140. In some aspects, the oculometric parameters include parameters such as (i) a pupil center 176, (ii) a pupil radius 178, (iii) an iris radius 174, (iv) an iris translation 172, and (v) an iris rotation 170. The pupil center 176 is a center of the pupil and may be represented using coordinates (e.g., three-dimensional (3D) lateral displacement vector (x,y,z)) that identifies a location of the pupil center in a coordinate system. The pupil radius 178 may be a radius of the pupil and may be represented as a scalar with distance units. The iris translation 172 (or iris translation 160) is a center of the iris and may be represented using coordinates (e.g., 3D lateral displacement vector (x,y,z)) that identify a location of the iris center in a coordinate system. The iris radius 174 (or iris radius 162) may be a radius of the iris and may be represented as a scalar with distance units. In some aspects, the iris radius 174 is assumed to have a small variance in the human population (e.g., 5%-15% considering iris radius varies from 11 mm-13 mm among the human population). The iris rotation 170 (or iris rotation 158) is representative of a rotation of the iris and is retrieved as the iris normal vector (e.g., perpendicular to the iris circle plain). In some aspects, the iris rotation 170 may be projected to a 3D vector in a device coordinate system (e.g., x, y, z) or represented by a 2D vector in a head coordinate system (e.g., azimuth angle and elevation angle). In some aspects, the OPS 114 may obtain the coordinates of the oculometric parameters in one or more coordinate systems, such as the device coordinate system or the head coordinate system illustrated in FIGS. 3A and 3B, respectively.

Figure 3A:
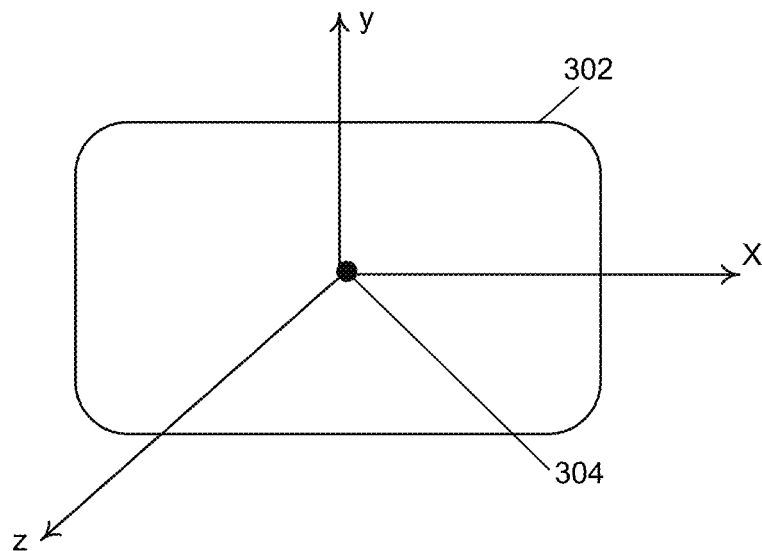
FIG. 3A illustrates a device coordinate system, according to some embodiments.

FIG. 3A illustrates a device coordinate system, consistent with various embodiments. In some aspects, the device coordinate system is a Cartesian coordinate system, with a center of a display 302 of a client device (e.g., the client device 106) considered as an origin 304 having the (x,y,z) coordinates as (0,0,0). The device coordinate system defines the three orthogonal axes, e.g., x-axis in the direction of the horizontal edge of the display 302, y-axis in the direction of the vertical edge of the display 302 and perpendicular to the x-axis, and z-axis in a direction perpendicular to the plane of the display 302.

For the medical purpose of measuring gaze to track the status of mental health and neurological disorder, gaze direction is generally measured relative to the skull of the user in which are anchored the extraocular muscles that move the eyeball in the socket.

Figure 3B:
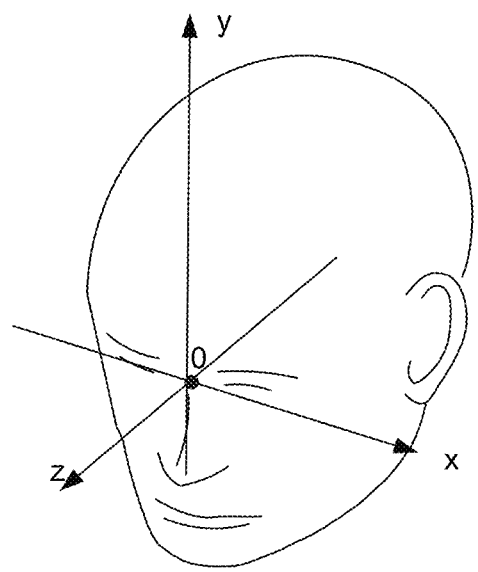
FIG. 3B illustrates a head coordinate system, according to some embodiments.

FIG. 3B shows a 3D coordinate system for measuring gaze relative to the skull, according to some embodiments. The x-axis is a line through the centroids of both irises. The origin is marked 0 in FIG. 3B. The origin is on the x-axis halfway between the centroids of both irises. The vertical y-axis is defined by the chin and forehead rest in laboratory setup or through a calibration processes. The z-axis is perpendicular to both x- and y-axes. In addition, the z-coordinate may be corrected using additional information collected from multiple images (and angles) during measurement.

Referring to the OPS 114, the OPS 114 may be configured to represent the coordinates of the oculometric parameters in any of the coordinate systems, including the head coordinate system or the device coordinate system. Further, the OPS 114 may be configured to convert the coordinates from one coordinate system to another, such as from the head coordinate system to the device coordinate system or vice versa.

The OPS 114 may also obtain eyelid data 164, such as coordinates of the upper eyelid boundary and lower eyelid boundary of both the eyes. The eyelid data 164 may be used in determining, or in improving the accuracy of, the oculometric parameters. In some aspects, the OPS 114 may obtain the above data (e.g., oculometric parameters 170-178, eyelid data 164 or other data) as time series data. For example, the OPS 114 may extract a first set of values of the oculometric parameters 170-178 for a first moment in time of the video stream 125, a second set of values of the oculometric parameters 170-178 for a second moment in time of the video stream 125 and so on. That is, the OPS 114 may continuously extract the oculometric parameters 170-178 at a specified time interval (e.g., every millisecond, every few milliseconds, or other temporal resolution). Further, the OPS 114 may obtain the above data for one or both the eyes 145 of the user 140.

The OPS 114 may perform several processes to extract the above oculometric parameters (e.g., oculometric parameters 170-178) from the preprocessed video stream 151. For example, in an extraction process 192, the OPS 114 may obtain a first set of oculometric parameters, such as iris data 153, eyelid data 155, and pupil center 157. In some aspects, the OPS 114 may use computer vision techniques on the preprocessed video stream 151 to model the translation and rotation of a face of the user 140 with respect to the camera 120 and to identify the eyes and the mouth in the face. After identifying the position of the eyes, the OPS 114 may obtain the eyelid data 155 (e.g., coordinates of an array of points that describe a polygon representing the eyelids) for each frame (e.g., using the fact that their edge may be approximated with quadratic functions). In some aspects, the OPS 114 may determine the iris data 153 (e.g., a shape, such as an ellipsoid, representing the iris) by determining the pixels that are in or out of the iris radius at any moment in time based on the eyelid's location as a time series. In some aspects, the OPS 114 may be configured to consider that the iris and pupil are ellipsoids with a relatively uniform and dark color compared to the sclera (e.g., the white part of the eye) in determining the pixels that are in or out. The iris data 153 may include several coordinates such as a first coordinate and a second coordinate, which correspond to right and left coordinates of a shape representing the iris (e.g., an ellipse); a third coordinate and fourth coordinate, which correspond to top and bottom coordinates of the shape; and a fifth coordinate corresponding to a center of the iris. The pupil center 157 may also be determined based on the time series of the eyelid data 155 and iris data 153. In some aspects, the pupil center 157 may include a coordinate representing a location of the center of the pupil.

In some aspects, the OPS 114 may implement a prediction model in the extraction process 192 and may obtain the first set of oculometric parameters via the prediction model (e.g., based on the video stream 125 or the preprocessed video stream 151). As an example, the OPS 114 may input the video stream 125 or the preprocessed video stream 151 to the prediction model, which then outputs the first set of oculometric parameters. In some aspects, the system 100 may train or configure a prediction model to facilitate the generation of the first set of oculometric parameters. In some aspects, system 100 may obtain a video stream having a video of the face of a user (e.g., video stream 125 or preprocessed video stream 151) and provide such information as input to a prediction model to generate predictions (e.g., first set of oculometric parameters such as iris data, eyelid data, pupil center, etc.). System 100 may provide a reference feedback to the prediction model and the prediction model may update one or more portions of the prediction model based on the predictions and the reference feedback. As an example, where the prediction model generates predictions based on the video stream 125 or the preprocessed video stream 151, the first of oculometric parameters associated with such input video streams may be provided as the reference feedback to the prediction model. As an example, a particular set of oculometric parameters may be verified as an appropriate set of oculometric parameters (e.g., via user confirmation of the set of oculometric parameters, via one or more subsequent actions demonstrating such goal, etc.). The foregoing user input information may be provided as input to the prediction model to cause the prediction model to generate predictions of the first set of oculometric parameters, and the verified set of oculometric parameters may be provided as reference feedback to the prediction model to update the prediction model. In this way, for example, the prediction model may be trained or configured to generate more accurate predictions.

In some aspects, the foregoing operations for updating the prediction model may be performed with a training dataset with respect to one or more users (e.g., a training dataset associated with a given user to specifically train or configure the prediction model for the given user, a training dataset associated with a given cluster, demographic, or other group to specifically train or configure the prediction model for the given group, a training dataset associated with any given set of users, or other training dataset). As such, in some aspects, subsequent to the updating of the prediction model, system 100 may use the prediction model to facilitate generation of a first set of oculometric parameters.

In some aspects, the OPS 114 may also further adjust, modify, or correct the first set of parameters based on other factors, such as optometric data associated with a user. For example, the user 140 may have certain vision conditions such as myopia, hyperopia, astigmatism, or other vision conditions and the user may wear corrective lenses such as eyeglasses or contact lens. The OPS 114 may consider such optometric conditions of the user 140 and correct, adjust or modify, values of one or more of the first set of oculometric parameters. In some aspects, the OPS 114 may obtain the optometric data associated with the user 140 from user profile data (e.g., stored in the database 132).

In some aspects, the OPS 114 may further process 193 the iris data 153 to extract iris related parameters such as iris rotation 158, iris translation 160, and iris radius 162. In some aspects, the above iris related parameters are obtained using an ML technique. For example, the OPS 114 may implement a maximum likelihood estimation (MLE) based curve fitting method to estimate the iris related parameters. The iris data is provided as input to the MLE-based curve fitting method (e.g., oval fit-based on an assumption that iris is circular and so when projected to a 2D plane it is oval/ellipse), which generates the above iris related parameters. In some aspects, in statistics, MLE is a method of estimating the parameters of a probability distribution by maximizing a likelihood function, so that under the assumed statistical model the observed data is most probable. The point in the parameter space that maximizes the likelihood function is called the maximum likelihood estimate. In some aspects, curve fitting operation is a process of constructing a curve, or mathematical function, that has the best fit to a series of data points, subject to constraints (e.g., oval fit). Curve fitting may involve either interpolation, where an exact fit to the data is required, or smoothing, in which a "smooth" function is constructed that approximately fits the data. Fitted curves may be used as an aid for data visualization, to infer values of a function where no data are available, and to summarize the relationships among two or more variables.

In some aspects, by performing the MLE-based curve fitting operation the accuracy of at least some of the iris related parameters may be further improved. For example, the shape depicting the iris boundary is further improved from the coordinates of the shape in the iris data 153, and therefore an improved or more accurate iris radius 162 may be determined. In some aspects, the iris translation 160, also referred to as iris center, is similar to the coordinates of the iris center in the iris data 153. In some aspects, in the process 193, the OPS 114 may consider different iris centers, construct an iris shape for each of the candidate iris centers, and assign a confidence score for each of the shapes. Such a method may be repeated for different iris centers, and the shape having a score satisfying a score criterion (e.g., the best score) is selected. In some aspects, the score for each iteration may reflect a log-likelihood of the examined parameter set (e.g., coordinates of the iris shape, radius and center), based on the known physical constraints and assumptions. In some aspects, the physical constraints and assumptions may improve the efficiency of the MLE process by introducing better estimated initial conditions before iterating towards convergence. For example, some assumptions may include that: the iris is circular (which when projected on a plane as 2D is represented as ellipse/oval), iris center is expected at the centroid of the circles, high contrast between iris and sclera, degree of similarity of orientation between left and right eye, stimulus-based assumption on the expected gaze point, and brightness of a display of the client device on which a video stimulus is shown to the user. In some aspects, examples of physical constraints may include: pupil dilation dependence in overall brightness (light conditions), limited range of face orientation as users look at the display, blinking may initiate uncertainty due to readjustment time, or physical possible range of motion (both face and eyeball).

The OPS 114 may perform a deconvolution process 194 on the video stream 125 or the preprocessed video stream 151 to adjust (e.g., improve the resolution or increase the accuracy of) some oculometric parameters, such as the eyelid data 155 and pupil center 166, and determine other oculometric parameters, such as the pupil radius. In some aspects, the OPS 114 may perform a blind deconvolution process to improve the accuracy of the oculometric parameters. In image processing, blind deconvolution is a deconvolution technique that permits recovery of the target scene from a single or a set of "blurred" images in the presence of a poorly determined or unknown point spread function (PSF). Regular linear and non-linear deconvolution techniques may utilize a known PSF. For blind deconvolution, the PSF is estimated from the image or image set, allowing the deconvolution to be performed. Blind deconvolution may be performed iteratively, whereby each iteration improves the estimation of the PSF and the scene, or non-iteratively, where one application of the algorithm, based on exterior information, extracts the PSF. After determining the PSF, the PSF may be used in deconvolving the video stream 125 or the preprocessed video stream 151 to obtain the adjusted oculometric parameters (e.g., adjusted eyelid data 164, adjusted pupil center 166, or pupil radius 168).

In some aspects, applying blind deconvolution algorithm may help in decreasing or removing the blurring in the images/video. The deconvolution process may be repeated one or more times to obtain adjusted oculometric parameters (e.g., whose accuracy or resolution is improved compared to oculometric parameters prior to the deconvolution process 194). In some aspects, the irradiance may be estimated based on relative brightness of the sclera with respect to the iris/pupil. The irradiance may be indicative of the illuminance that the user is subject to from the user device and/or the environment.

In some aspects, in determining the PSF, the blind deconvolution process considers various factors. For example, the OPS 114 may input (a) the video stream 125 or the preprocessed video stream 151 (e.g., which is a time-series image sequence) with high temporal resolution (e.g., equal to or faster than 30 ms per frame); (b) stimulus data such as spatio-temporal information on a stimulus presented on the display of the client device 106, and optical properties information on the of the stimulus, including spectral properties (e.g., color) and intensity (e.g., brightness); (c) environment data such as lighting in the environment (e.g., a room) where the user is located, which can be measured using information obtained from the camera 120, (d) device data such as orientation information of the client device 106, information from one or more sensors associated with the client device 106 such as acceleration sensors. Such factors help in efficient calculation of the PSF, minimizes the noise uncertainty, leading to better accuracy in the overall deconvolution.

In some aspects, the deconvolution process 194 is integrated with an MLE process to further improve the accuracy of the oculometric parameters. For example, the MLE process may be used to improve the accuracy of the eyelid data 155. As described above, the eyelid data 155 includes coordinates of an array of points that describe a shape (e.g., polygon) of the eyelids. The MLE process performs a parabolic curve fitting operation on the eyelid data 155 with a constraint that the eyelids are parabolic in shape to obtain a more accurate representation of the eyelids, as the adjusted eyelid data 164. In some aspects, the adjusted eyelid data 164 may include coordinates of a collection of points that describe a shape (e.g., parabolic) of an eyelid. Such adjusted eyelid data 164 may be obtained for both eyelids of the eye and for both eyes. In some aspects, the OPS 114 may use the adjusted eyelid data 164 information to predict the precise oculometric parameter values, such as the pupil radius center, even when some are physically challenging (e.g., when the upper eyelid covers the pupil center, or when only some of the iris is exposed to the camera).

In some aspects, the MLE process may also be used for obtaining or improving pupil related data, such as pupil radius 168. In some aspects, by performing the MLE-based curve fitting operation the accuracy of the pupil related data may be further improved. In some aspects, in the MLE process, the OPS 114 may consider different pupil centers, construct a pupil shape for each of the candidate pupil centers, and assign a confidence score for each of the shapes. Such a method may be repeated for different pupil centers, and the shape having a score satisfying a score criterion (e.g., the best score) is selected. Once the shape is selected, the corresponding center is selected as the adjusted pupil center 166 and the pupil radius 168 may be determined based on the selected shape and the adjusted pupil center 166. In some aspects, the score for each iteration may reflect a log-likelihood of the examined parameter set (e.g., pupil radius and center), based on the known physical constraints and assumptions. In some aspects, the physical constraints and assumptions may improve the efficiency of the MLE process by introducing better estimated initial conditions before iterating towards convergence. For example, some assumptions may include that: the pupil is circular (which when projected on a 2D plane is represented as ellipse/oval), pupil center is expected at the centroid of the circle, degree of similarity of orientation between left and right eye, stimulus-based assumption on the expected gaze point, and brightness of a display of the client device on which a video stimulus is shown to the user. In some aspects, examples of physical constraints may include: pupil dilation dependence in overall brightness (light conditions), limited range of face orientation as users look at the display, blinking may initiate uncertainty due to readjustment time, or physical possible range of motion (both face and eyeball). Accordingly, the OPS 114 may obtain adjusted oculometric parameters, such as the adjusted eyelid data 164, adjusted pupil center 166, and the pupil radius 168 from the deconvolution process 194. In some aspects, the above process 193 of processing iris data and the deconvolution process 194 may output the following oculometric parameters: adjusted eyelid data 164, adjusted pupil center 166, pupil radius 168, iris rotation 158, iris translation 160, and iris radius 162 (also referred to as "a first set of oculometric parameters") in a first resolution. For example, the first resolution may be at a pixel level or other lower resolution.

In some aspects, the OPS 114 may further improve the resolution of the first set of oculometric parameters. For example, the OPS 114 may improve the resolution from the first resolution to a second resolution (e.g., 0.1 mm, sub-pixel level or some other resolution that is greater than the first resolution). In some aspects, the OPS 114 may input the first set of oculometric parameters to an improve resolution process 195 to obtain a second set of oculometric parameters (e.g., oculometric parameters 170-178) at the second resolution. In some aspects, the improve resolution process 195 may obtain the second set of oculometric parameters via a prediction model (e.g., based on the first set of oculometric parameters). As an example, the OPS 114 may input the first set of oculometric parameters obtained at the first resolution to the prediction model, which then outputs the second set of oculometric parameters at the second resolution. In some aspects, the system 100 may train or configure a prediction model to facilitate the generation of the second set of oculometric parameters. In some aspects, system 100 may obtain input data such as (a) a video stream having a video of the face of a user (e.g., video stream 125 or preprocessed video stream 151), (b) the first set of oculometric parameters (obtained at a first resolution as described above), (c) environment data such as lighting in the environment (e.g., a room) where the user is located, which can be measured using information obtained from the camera 120, (d) device data such as a display size, display resolution, display brightness, or display contrast associated with a display of the client device 106, model and manufacturer information of the camera 120, or (e) user information such as demographic, clinical history, optometric data, etc.

The system 100 may provide such input data to a prediction model to generate predictions (e.g., the second set of oculometric parameters such as iris rotation 170, iris translation 172, iris radius 174, pupil center 176, and pupil radius 178 at a second resolution). System 100 may provide reference feedback to the prediction model and the prediction model may update one or more portions of the prediction model based on the predictions and the reference feedback. As an example, where the prediction model generates predictions based on the above input data, a second set of oculometric parameters associated with such input data may be provided as a reference feedback to the prediction model. As an example, a particular set of oculometric parameters obtained at the second resolution may be verified as an appropriate set of oculometric parameters (e.g., via user confirmation of the set of oculometric parameters, via one or more subsequent actions demonstrating such goal, etc.). The foregoing user input information may be provided as input to the prediction model to cause the prediction model to generate predictions of the second set of oculometric parameters, and the verified set of oculometric parameters may be provided as a reference feedback to the prediction model to update the prediction model. In this way, for example, the prediction model may be trained or configured to generate more accurate predictions. In some aspects, the reference feedback having the oculometric parameters at the second resolution may be obtained, determined or derived from information obtained using any of several eye tracking devices that produce oculometric parameters at a high resolution (e.g., the second resolution). For example, some tracking devices produce oculometric parameters such as gaze origin, gaze point and pupil diameter at the second resolution. The OPS 114 may derive the second set of oculometric parameters such as the iris rotation, iris translation, iris radius, pupil center, and pupil radius from the oculometric parameters generated using the eye tracking device and provide the derived second set of oculometric parameters as reference feedback to train the prediction model. Such reference feedback may be obtained for several videos and provided as training dataset to train the prediction model.

In some aspects, the foregoing operations for updating the prediction model may be performed with a training dataset with respect to one or more users (e.g., a training dataset associated with a given user to specifically train or configure the prediction model for the given user, a training dataset associated with a given cluster, demographic, or other group to specifically train or configure the prediction model for the given group, a training dataset associated with any given set of users, or other training dataset). As such, in some aspects, subsequent to the updating of the prediction model, system 100 may use the prediction model to facilitate generation of a first set of oculometric parameters.

In some aspects, the OPS 114 may also extract additional oculometric parameters such as a pupil visible fraction, a pupil coverage asymmetry, iris visible fraction, or iris coverage asymmetry. In some aspects, the pupil visible fraction is calculated as the ratio between the pupil area not covered by the eyelids and the pupil iris area. The pupil coverage asymmetry may be defined as the mean of the pupil upper eyelid covered fraction and the pupil lower eyelid covered fraction when the upper eyelid covered fraction is represented in a positive value, and the lower eyelid covered fraction is represented in a negative value, normalized by the iris total covered area. The values of this parameter may vary between −1 and 1 and project the asymmetry between the eyelid coverage of the upper and the lower eyelids (e.g., "−1" may denote that all covered area is covered by the lower eyelid, "1" may denote that all covered area is covered by the upper eyelid, and "0" may denote that the upper and lower eyelids cover equal areas).

The OPS 114 may extract the additional oculometric parameters based on the second set of oculometric parameters 170-178. For example, the OPS 114 may perform geometrical projections and calculations using the second set of oculometric parameters 170-178 to determine the additional oculometric parameters.

In some aspects, the OPS 114 may also extract, generate, or derive the eye movement parameters (e.g., pupillary response parameters and gaze parameters) that are indicative of eye movements responsive to a non-standard stimulus (e.g., a video or image displayed on the client device 106). The eye movement parameters may be derived using the second set of oculometric parameters (e.g., obtained as described above). In some aspects, the pupillary response parameter is indicative of a response of the eye to a particular stimulus, and the gaze parameters are indicative of where the eyes are focused or looking. The OPS 114 may obtain different types of gaze parameters, such as fixation, saccade, pursuit, or another gaze parameter. In some aspects, fixation is defined as the distribution of eye movements while inspecting a specific area of the stimulus. In some aspects, saccade is defined as the distribution of eye movements between inspection areas. In some aspects, pursuit is defined as the distribution of eye movements while following movement. These eye movement parameters may be used in generating various digital markers (e.g., digital biomarkers).

In some aspects, the marker subsystem 116 may produce digital markers (e.g., parameters) that may act as an indicator of one or more neurological disorders. The marker subsystem 116 may produce the digital markers based on the oculometric parameters or the eye movement parameters (e.g., discussed above). In some aspects, these digital markers are tightly correlated (and can therefore serve as proxies) for disease progression or acuity. The digital markers generated by the marker subsystem 116 may be objective, sensitive, accurate (0.1 mm or less), or correlated with clinical progression of diseases, and may be obtained remotely, outside of lab settings and even in a distributed manner.

Note that the oculometric parameters, the eye movement parameters, or the digital markers may be obtained in real-time (e.g., based on a real-time video stream obtained from the camera 120) or offline (e.g., using a video stored in the database 132). Further, the oculometric parameters (e.g., second set of oculometric parameters 170-178 or other oculometric parameters) are obtained as time-series data and for one or more eyes of the user. That is, the oculometric parameters 170-178 may be extracted continuously at a specified time interval (e.g., every millisecond, every few milliseconds, or other temporal resolution).

In some aspects, the prediction models described above may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some aspects, each individual neural unit may have a summation function which combines the values of all its inputs together. In some aspects, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some aspects, neural networks may include multiple layers (e.g., where a signal path traverses from front layers to back layers). In some aspects, back propagation techniques may be utilized by the neural networks, where forward stimulation is used to reset weights on the "front" neural units. In some aspects, stimulation and inhibition for neural networks may be more free-flowing, with connections interacting in a more chaotic and complex fashion.

A neural network may be trained (i.e., whose parameters are determined) using a set of training data (e.g., ground truths). The training data may include a set of training samples. Each sample may be a pair comprising an input object (typically an image, a measurement, a tensor or vector which may be called a feature tensor or vector) and a desired output value (also called the supervisory signal). A training algorithm analyzes the training data and adjusts the behavior of the neural network by adjusting the parameters (e.g., weights of one or more layers) of the neural network based on the training data. For example, given a set of N training samples of the form $\{(x_1, y_1), (x_2, y_2), \ldots (x_N, y_N)\}$ such that $x_i$ is the feature tensor/vector of the i-th example and $y_i$ is its supervisory signal, a training algorithm seeks a neural network g: X→Y, where X is the input space and Y is the output space. A feature tensor/vector is an n-dimensional tensor/vector of numerical features that represent some object (e.g., a complex electric field image). The tensor/vector space associated with these vectors is often called the feature or latent space. After training, the neural network may be used for making predictions using new samples.

Figure 2:
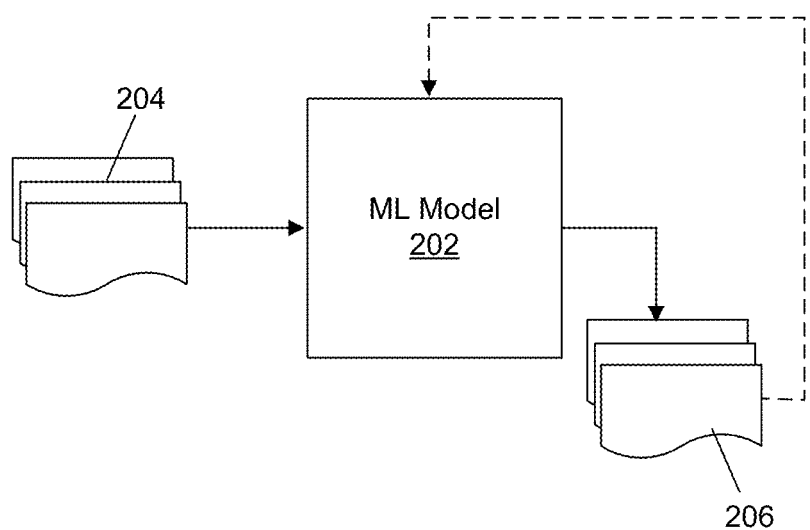
FIG. 2 shows a machine learning model configured to facilitate prediction of oculometric parameters, according to some embodiments.

As an example, with respect to FIG. 2, machine learning model 202 may take inputs 204 and provide outputs 206. In one use case, outputs 206 may be fed back to machine learning model 202 as input to train machine learning model 202 (e.g., alone or in conjunction with user indications of the accuracy of outputs 206, labels associated with the inputs, or with other reference feedback information). In another use case, machine learning model 202 may update its configurations (e.g., weights, biases, or other parameters) based on its assessment of its prediction (e.g., outputs 206) and reference feedback information (e.g., user indication of accuracy, reference labels, or other information). In another use case, where machine learning model 202 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 202 may be trained to generate better predictions.

Figure 4:
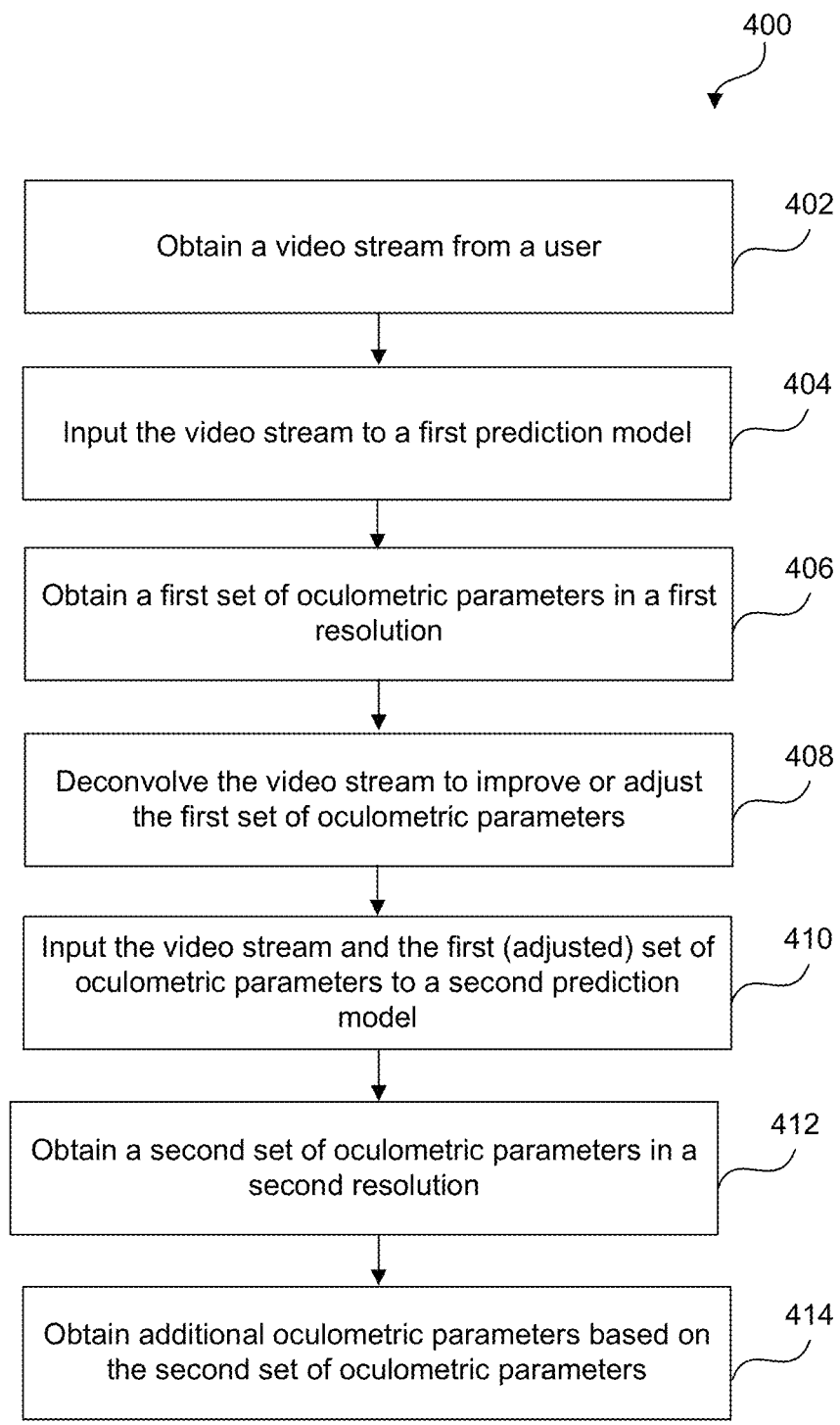
FIG. 4 is a flow diagram of a process for obtaining oculometric parameters at a high resolution, according to some embodiments.

FIG. 4 is a flow diagram of a process 400 for obtaining oculometric parameters at a high resolution, consistent with various embodiments. In some aspects, the process 400 may be executed in the system 100 of FIG. 1A.

In an operation 402, a video stream is obtained from a client device associated with a user. The video stream may include a video of a face of the user. For example, the video stream 125 is obtained from the client device 106. In some aspects, the video stream may be obtained in real-time from the client device, e.g., capture by a camera associated with the client device such as the camera 120 of the client device 106, or may be a recorded video that is obtained from a data storage device, e.g., database 132, data storage or a memory on the client device, or other data storage devices.

In an operation 404, the video stream is input to a first prediction model to obtain a first set of oculometric parameters. In some aspects, the video stream may pre-processed prior to being input to the first prediction model. In some aspects, preprocessing the video stream may include performing an ETL process on the video stream to adjust color and brightness (e.g., white balance) in the video stream, reduce noise from the video stream, improve resolution of the video stream by implementing one or more multi-frame super-resolution techniques, or other such video processing. For example, the video stream input to the first prediction model may be the video stream 125 or the preprocessed video stream 151.

In an operation 406, the first set of oculometric parameters are obtained from the first prediction model. The oculometric parameters correspond to various characteristics of an eye. For example, the first set of oculometric parameters may include iris data, eyelid data, and pupil center. The iris data may include coordinates of several points that describe a center and a shape (e.g., an ellipse) of the iris. The eyelid data may include coordinates of an array of points that describe a shape (e.g., a polygon) representing the eyelids. The pupil center may include a coordinate of a point representing the center of the pupil. In some aspects, the first set of oculometric parameters are obtained at a first resolution. For example, the first resolution may be at a pixel level or other lower resolution. In some aspects, the iris data is further processed to obtain iris rotation, iris translation, and iris radius from the iris data. For example, the iris data 153 is processed to obtain the iris rotation 158, iris translation 160, and iris radius 162. The iris rotation may be representative of a rotation of the iris and may be retrieved as the iris normal vector (e.g., perpendicular to the iris circle plain). The iris translation may be a center of the iris and may be represented using coordinates that identify a location of the iris center. The iris radius may be a radius of the iris and may be represented as a scalar with distance units. In some aspects, an MLE-based curve fitting method may be performed to estimate the iris related parameters. The iris data is provided as input to the MLE-based curve fitting method (e.g., oval fit), which generates the above iris related parameters.

In an operation 408, the video stream is deconvolved to adjust (e.g., improve accuracy or resolution) the first set of oculometric parameters. The video stream input to the deconvolution process may be the video stream 125 or the preprocessed video stream 151. In some aspects, the video stream is deconvolved by using a blind deconvolution process integrated with an MLE process, the additional details of which are described above at least with reference to FIGS. 1A and 1B and below at least with reference to FIG. 5. In some aspects, applying blind deconvolution algorithm may help in decreasing or removing the blurring in the images/video, or any other noise from the video stream to improve the accuracy of the oculometric parameters extracted. The deconvolution process may be repeated one or more times to obtain the adjusted oculometric parameters (e.g., whose accuracy or resolution is improved compared to the oculometric parameters prior to the deconvolution process). The adjusted parameters may include adjusted eyelid data, adjusted pupil center and pupil radius.

In an operation 410, the video stream and the first set of parameters are input to a second prediction model to obtain the oculometric parameters at a high resolution. For example, the first set of oculometric parameters, including the iris rotation 158, iris translation 160, the iris radius 162, the adjusted eyelid data 164, adjusted pupil center 166 and pupil radius 168, etc. are input to the second prediction model. In some aspects, the second prediction model is trained to predict the set of oculometric parameters at a high resolution. For example, the second prediction model is trained with several training datasets in which each dataset includes a video of the face of the user, device data of the client device, environment data of an environment in which the user is located and user information of the user as input data, and the corresponding set of oculometric parameters at a high resolution as the ground truth. In some aspects, the set of oculometric parameters at the high resolution is obtained using one or more eye tracking devices that are configured to produce the oculometric parameters at a high resolution.

In an operation 412, a second set of oculometric parameters are obtained at a second resolution from the second prediction model. For example, the second set of oculometric parameters including iris rotation 170, iris translation 172, iris radius 174, pupil center 176, and pupil radius 178 are obtained at a second resolution (e.g., 0.1 mm, sub-pixel level or some other resolution greater than the first resolution).

Optionally, in an operation 414, additional set of oculometric parameters may be obtained. For example, additional oculometric parameters such as a pupil visible fraction, a pupil coverage asymmetry, iris visible fraction, or iris coverage asymmetry may be obtained based on the second set of oculometric parameters. The OPS 114 may obtain the addition oculometric parameters by performing geometrical projections and calculations using the second set of oculometric parameters. In some aspects, the pupil visible fraction is calculated as the ratio between the pupil area not covered by the eyelids and the pupil iris area. The pupil coverage asymmetry may be defined as the mean of the pupil upper eyelid covered fraction and the pupil lower eyelid covered fraction when the upper eyelid covered fraction is represented in a positive value, and the lower eyelid covered fraction is represented in a negative value, normalized by the iris total covered area. The values of this parameter may vary between −1 and 1 and project the asymmetry between the eyelid coverage of the upper and the lower eyelids (e.g., "−1" may denote that all covered area is covered by the lower eyelid, "1" may denote that all covered area is covered by the upper eyelid, and "0" may denote that the upper and lower eyelids cover equal areas.

Operations 402-414 may be performed by a subsystem that is the same as or similar to OPS 114, in accordance with one or more embodiments.

Figure 5:
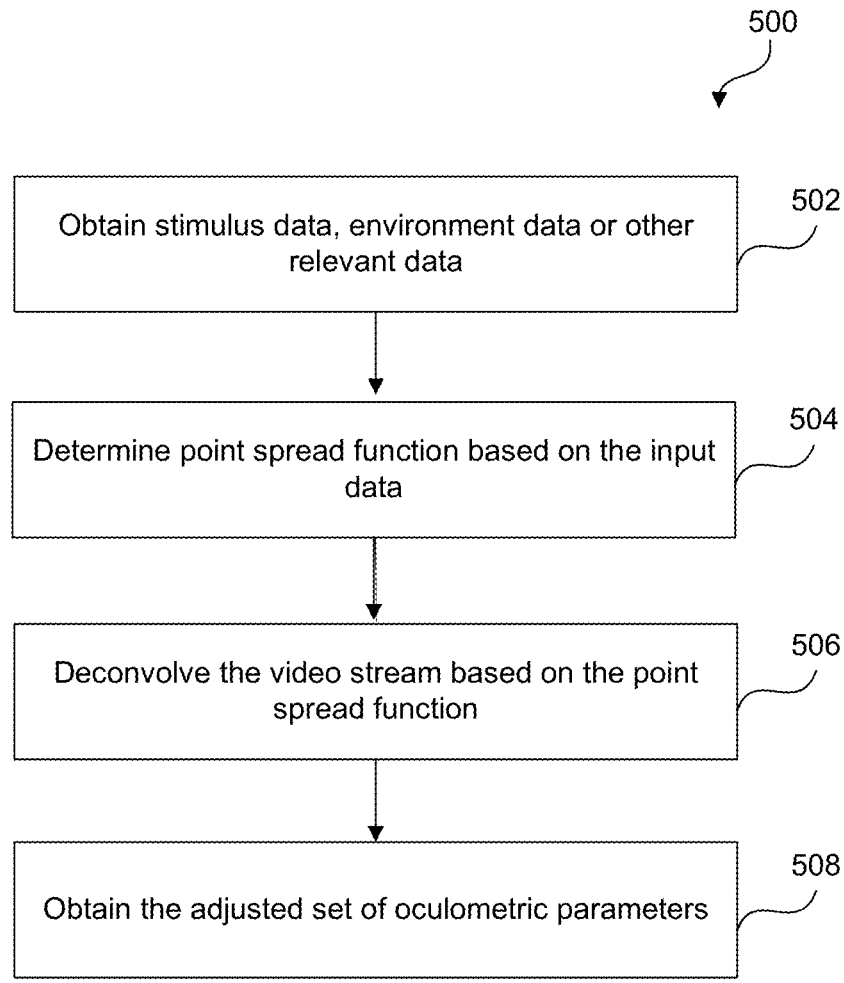
FIG. 5 is a flow diagram of a process for deconvolving a video stream to obtain adjusted oculometric parameters, according to some embodiments.

FIG. 5 is a flow diagram of a process 500 for deconvolving a video stream to obtain adjusted oculometric parameters, consistent with various embodiments. In some aspects, the process 500 may be performed as part of operation 408 of process 400.

In an operation 502, input data such as the video stream, stimulus data, environment data, device data, or other data is obtained to perform deconvolution of the video stream. The video stream input to the deconvolution process may be the video stream 125 or the preprocessed video stream 151. The stimulus data may include spatio-temporal information on a stimulus presented on the display of the client device 106, or optical properties information of the stimulus, including spectral properties (e.g., color) and intensity (e.g., brightness). The environment data may include information such as lighting in the environment (e.g., a room) in which the user is located. For example, the lighting may include a range (i.e., minimum lightness value to a maximum lightness value). The device data may include information such as orientation information of the client device 106, information from one or more sensors associated with the client device 106 such as acceleration sensors. Further, the input data may also include eyelid data (e.g., eyelid data 155) and the pupil center (e.g., pupil center 157).

In an operation 504, a point spread function of the blind deconvolution algorithm is determined based on the input data.

In an operation 506, the video stream is deconvolved based on the point spread function. The deconvolution process removes or reduces any blurring, or any other noise introduced into the video stream due to user environment related factors, client device related factors, camera related factors, video stimulus related factors etc. to improve the video stream and therefore, improve the accuracy of the oculometric parameters retrieved.

In an operation 508, the adjusted oculometric parameters are derived from the deconvolved video stream as described above. For example, the adjusted oculometric parameters may include adjusted eyelid data 164, adjusted pupil center 166, or pupil radius 168. In some aspects, the deconvolution process is integrated with an MLE process to further improve the accuracy of the oculometric parameters. For example, the MLE process may be used to improve the accuracy of the eyelid data 155. The MLE process may be used to perform a parabolic curve fitting operation on the eyelid data 155 to obtain a more accurate representation of the eyelids, as adjusted eyelid data 164. In another example, the MLE process may be used to obtain or improve the accuracy of pupil related data, such as pupil radius 168. The MLE process may be used to perform a curve fitting operation (e.g., oval fit) to improve a shape of the pupil. For example, the MLE process may consider different pupil centers, and may construct a pupil shape for each of the candidate pupil centers and assign a confidence score for each of the shapes. Such a method may be repeated for different pupil centers, and the shape having a score satisfying a score criterion (e.g., the best score) is selected. Once the shape is selected, the corresponding center may be selected as the adjusted pupil center 166 and the pupil radius 168 may be determined based on the selected shape and the adjusted pupil center 166.

In some aspects, the process 500 may be repeated one or more times (e.g., until the accuracy or resolution of the oculometric parameters satisfy a criterion (e.g., exceed a threshold value) or the PSF satisfies a criterion) to improve the accuracy or resolution of the adjusted oculometric parameters.

In some aspects, the various computers and subsystems illustrated in FIG. 1A may include one or more computing devices that are programmed to perform the functions described herein. The computing devices may include one or more electronic storages (e.g., prediction database(s) 132, which may include training data database(s) 134 to store training data, model database(s) 136 to store prediction models, etc., or other electronic storages), one or more physical processors programmed with one or more computer program instructions, and/or other components. The computing devices may include communication lines or ports to enable the exchange of information within a network (e.g., network 150) or other computing platforms via wired or wireless techniques (e.g., Ethernet, fiber optics, coaxial cable, Wi-Fi, Bluetooth, near field communication, or other technologies). The computing devices may include a plurality of hardware, software, and/or firmware components operating together. For example, the computing devices may be implemented by a cloud of computing platforms operating together as the computing devices.

The electronic storages may include non-transitory storage media that electronically stores information. The storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some aspects, the processors may include a plurality of processing units. These processing units may be physically located within the same device, or the processors may represent processing functionality of a plurality of devices operating in coordination. The processors may be programmed to execute computer program instructions to perform functions described herein of subsystems 112-116 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-116 described herein is for illustrative purposes, and is not intended to be limiting, as any of subsystems 112-116 may provide more or less functionality than is described. For example, one or more of subsystems 112-116 may be eliminated, and some or all of its functionality may be provided by other ones of subsystems 112-116. As another example, additional subsystems may be programmed to perform some or all of the functionality attributed herein to one of subsystems 112-116.

Figure 6:
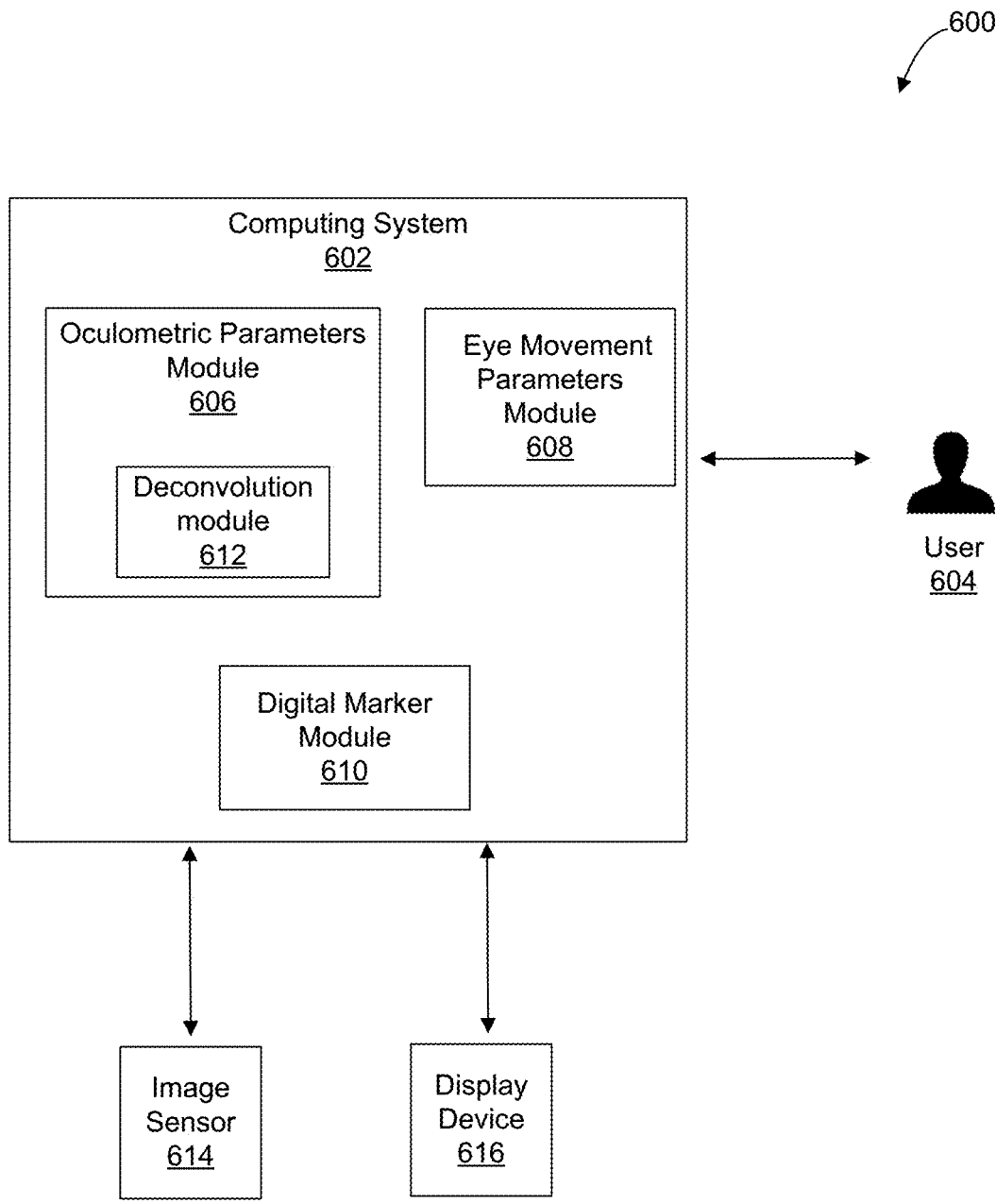
FIG. 6 is a block diagram of a system for determining oculometric parameters and determining one or more digital markers indicative of a neurological condition, according to some embodiments.

FIG. 6 is a block diagram of a system 600 for efficiently determining one or more digital markers indicative of a neurological condition, according to some embodiments.

System 600 may include a computing system 602. Computing system 602 may be coupled to an image sensor 614 and a display device 616. Computing system 602 may include an oculometric parameters module 606, an eye movement parameters module 608, and a digital marker module 610. Image sensor 614 may capture a video stream of a face of a user 604. The video stream may comprise a sequence of frames of an image of the face of the user). Computing system 602 may include a smartphone, a desktop computer, a server computer, and a cloud computing platform.

Oculometric parameters module 606 may determine one or more eye measurement parameters. The eye measurement parameters may include one or more oculometric parameters. As described previously herein, the oculometric parameters may include one or more of pupil center, pupil radius, iris radius, iris translation, and iris rotation for an eye or each of the eyes of user 604. In order to determine the one or more oculometric parameters, oculometric parameters module 606 may determine and track a location of the face and eye in the image frame. For example, oculometric parameters module 606 may use a facial recognition technique (e.g., deep learning) to identify a facial feature (e.g., an eye) in the image frame as would be understood by one of ordinary skill in the art. In some aspects, oculometric parameters module 606 may use an artificial neural network (ANN) such as a convolutional neural network (CNN), a recurrent neural network (RNN), a generative adversarial network (GAN), a radial basis function network (RNN), and the like. For example, oculometric parameters module 606 may identify the position of the eyes. The position of the eyes may be identified using computer vision techniques (e.g., based on pattern recognition, based on corneal reflection points, based on shape, based on dark and bright pupil effect, and/or based on an eye model) as would be understood by one of ordinary skill in the art.

After identifying the position of the eyes, oculometric parameters module 606 may generate a time series of information about the location of eyes in the field of view, the location of the face in the field of view, and/or the directional orientation of face in the field of view relative to the line of sight of the camera. For example, oculometric parameters module 606 may generate a first time series representing a location of the eye. As described previously herein, the time series may represent the location of one or both eyes at multiple moments in time in the video stream.

After locating the face and eye in the video stream, oculometric parameters module 606 may determine locations of eyelids, pupils, and/or irises using eye images. Oculometric module 606 may implement image segmentation methods and use the time series of information to separate the eye into a plurality of regions. The plurality of regions of the eye may include an eyelid region, a sclera region, a pupil region, and/or an iris region. Oculometric module 606 may determine the location of the pupil center, a pupil radius, an iris translation, and/or an iris rotation. The iris translation may refer to the 3D position (e.g., x,y,z coordinates in the coordinate system of FIG. 3A) of the center of the iris within the volume defined by the field of view of image sensor 614 and minimum and maximum working distances of image sensor 614. The iris rotation may refer to a measurement of eyeball rotation in the eye socket that is inferred from the shape of iris images. The determination of the locations of eyelids, pupils, and irises is further described in relation with FIG. 7.

A deconvolution module 612 may apply one or more deconvolution processes to the eye images. For example, deconvolution module 612 may use the time series representing the location of the eye to estimate the PSF of motion blur in the x and y directions. Then, the effect of the PSF may be reversed by deconvolution. The PSF may be estimated using a plurality of methods. For example, deconvolution module 612 may apply a modeling technique to derive a model as described in *Digital Image Processing*, Gonzalez and Woods, Pearson Education Limited, 2018, Section 5.6, "Estimating the Degradation Function: Estimation By Modeling").

After correcting for motion blur, the deconvolution module 612 may also apply a blind deconvolution process on the eye images to correct for blur caused by the PSF of image sensor 614. For example, deconvolution module 612 may generate a PSF. The generated PSF may be an estimate of the PSF of image sensor 614. As described previously herein in relation to FIG. 5, the deconvolution process may be applied iteratively to improve the accuracy of the oculometric parameters.

Eye movement module 606 may determine eye movement parameters from the eye measurement parameters. As described previously herein, the eye movements determined in response to external stimulus may be modeled as a signal processing system. The input signal to the signal processing system may be the changing output of display device 616. The output of the signal processing system may be the set of oculometric parameters determined by oculometric parameters module 606. The particular response of user 604 may be an impulse response function of the system. For example, the size of the pupil may change in response to light changes caused by display device 616, or other illumination source in an environment of user 604. In this case, the impulse response function may be referred to as a pupillary response function. For example, the pupillary response function may be expressed as:

$$P(t) = X(t)\left(e^{-at} + e^{-bt}\right) \quad (1)$$

and the pupil area as a function of time may be expressed as:

$$A(t) = (P*B)(t) \quad (2)$$

where t is the time, * is the convolution operator, B(t) is the brightness measured in the sclera in response to the light changes, and X(t) is a normal distribution function having expected value E(X) and variance $\sigma^2(X)$. E(X), $\sigma^2(X)$, a, and b may be taken to be linear functions of brightness, each having a slope and intercept. Thus, P(t) may be defined by eight parameters $p_{jk}$, where j=0, 1, 2, 3 and k=0, 1. $p_{jk}$ may be estimated using iterative blind deconvolution. Because P(t) may include brightness as an explicit independent variable, B(t) does not have to be a simple unchanging function, for example, a bright flash. As long as B(t) has a suitable brightness and is varying enough to be significantly changing the pupil size, the pupillary response function may be inferred from a variety of monitor displays (e.g., display device 616) and/or other sources of illumination.

The illumination may include ambient illumination and/or illumination from the monitor that the subject is observing.

In some aspects, the ambient illumination is expected to be stable. The monitor illumination may be expected to be strong enough to produce measurable changes in the brightness of the sclera in eye images. The total illumination may be expected to be not so strong as to effect very small pupil sizes nor so weak as to cause insufficient signal-to-noise ratio in the eye images In some aspects, a gaze tracking test may be performed. The two-dimensional direction of gaze may be determined based on the iris translation and/or iris rotation determined by the oculometric parameters module 606. In one example, the two-dimensional direction of gaze may be expressed as follows:

$$D(t) = (G*S)(t) \quad (3)$$

where t is time, * is the convolution operator, G(t) is a "gaze response function," S(t) is the "signal" embodied by a time series of targets displayed on display device 616.

The gaze response function may be an impulse response function that defines how a subject tracks various targets displayed on display device 616. In a non-limiting example, user 604 may be instructed to stare at a first target (e.g., a red dot) displayed on display device 616. For example, the image may comprise a solid background (e.g., a gray background) and a dot (e.g., a red dot). User 604 may be instructed to stare at the dot. The signal may be a constant background with a circular "plateau" region of constant height above the background (e.g., a circular shape having an attribute (e.g., color) different from the solid background). The signal may represent the place where the gaze is supposed to be. In some aspects, a measurement of a saccade may be performed in response to an abrupt change in a position of the target (e.g., the location of the dot is changed from a center of the display device to a side or edge of the display device). In another test, user 604 may be instructed to follow a smooth movement of the target across the solid background.

Because convolution is commutative, D(t)=(G*S)(t)=(S*G)(t), G(t) may be regarded as an input signal and S(t) may be regarded as an impulse response function. Therefore, the measured D(t) may be deconvolved using the known S(t) as the kernel to get G(t).

Digital marker module 610 may determine one or more digital markers based on the eye movement parameters. As described previously herein, the one or more digital markers (e.g., one or more biomarkers) may be indicative of one or more neurological conditions of user 604.

Figure 7:
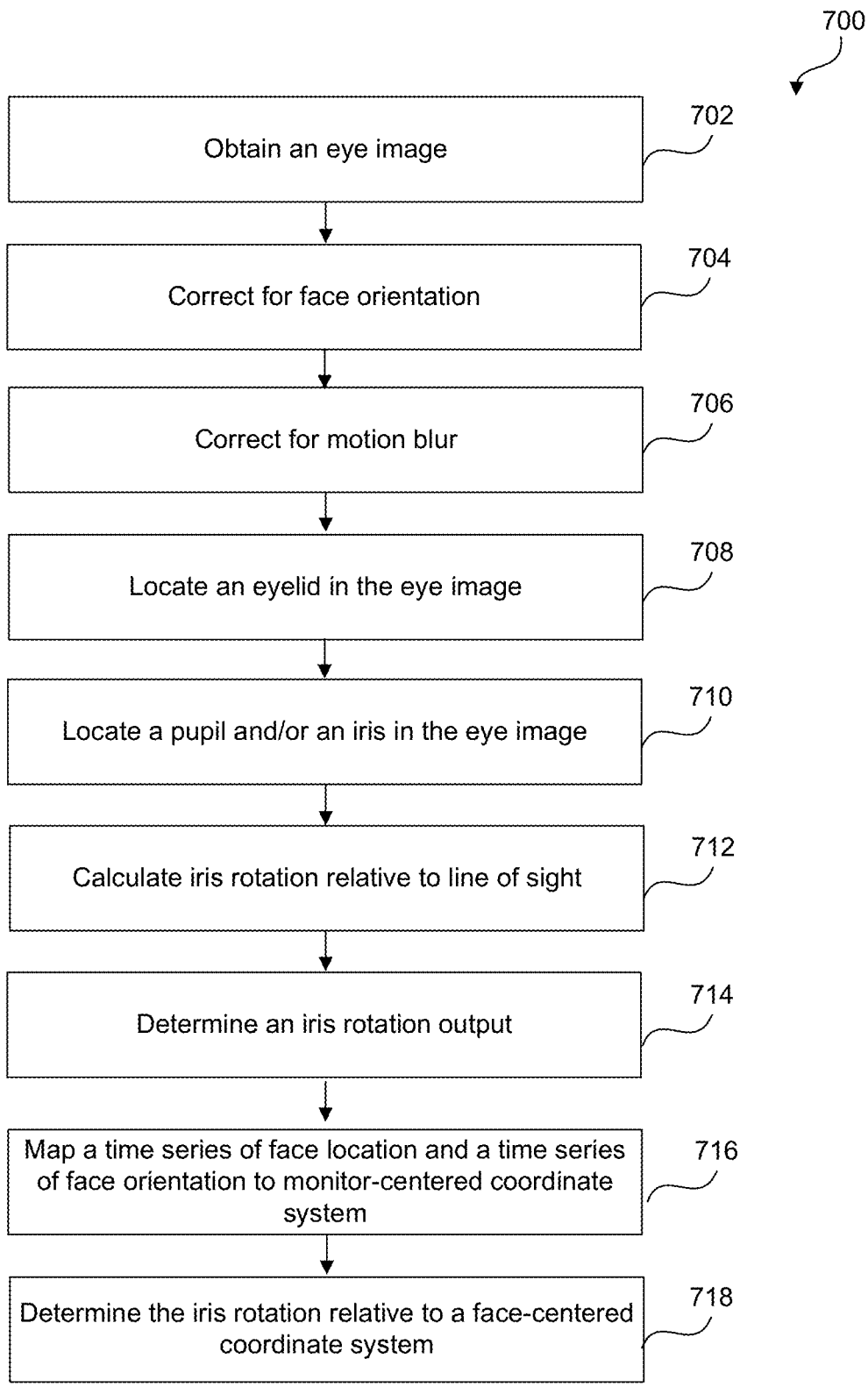
FIG. 7 is a flowchart for a method for determining a set of oculometric parameters, according to some embodiments.

FIG. 7 is a flowchart for a method 700 for determining a set of oculometric parameters, according to some embodiments. Method 700 can be performed by processing logic that can comprise hardware (e.g., circuitry, dedicated logic, programmable logic, microcode, and the like), software (e.g., instructions executing on a processing device), or a combination thereof. It is to be appreciated that not all steps may be needed to perform the disclosure provided herein. Further, some of the steps may be performed simultaneously, or in a different order than shown in FIG. 7, as will be understood by one of ordinary skill in the art.

Method 700 shall be described with reference to FIG. 6. However, method 700 is not limited to that example embodiment.

In 702, computing system 602 may obtain an eye image. For example, computing system 602 may crop from an image frame of a face of the user a region of interest. The image frame may be obtained from a video stream. The region of interest may include the eye of user 604 and an area surrounding the eye. In some aspects, computing device 602 may obtain two eye images corresponding to the two eyes of user 604. A first eye image may comprise a first eye of the user and the surrounding area. A second eye image may comprise a second eye of user 604 and the corresponding surrounding area.

In 704, computing system 602 may adjust an eye image to correct for the face orientation. The eye image may be corrected by affine transformation (e.g., rotation, scaling, and translation) to appear as it would if the user 604 was directly facing the image sensor 614. In some aspects, computing device 602 may determine a face orientation for each image frame and store the orientation in a time series. The time series of the face orientation may represent the face orientation in multiple successive image frames.

In 706, computing system 602 may correct for motion blur using deconvolution module 612. Deconvolution module 612 may compensate for motion blur as described above. For example, deconvolution module 612 may estimate a PSF of motion blur in the x and y directions. In some aspects, computing system 602 may use the time series of location of the eyes to calculate a spatial velocity used in the estimation of the PSF. The time series of location of the eyes may be generated by oculometric parameters module 606. The time series of location of the eyes represent the location of the eye in multiple successive image frames obtained from the video stream. In some aspects, computing system 612 may apply the modeling technique as described above to correct for motion blur. In some aspects, to correct for motion in the z direction, computing system 602 may resize each eye image in a time series of eye images so that they appear to be at a fixed range. The time series of eye images may represent a plurality of successive eye images obtained from the video stream. As discussed above, the iris radius 174 often has a small variance in the human population with a median size of about 12 mm (up to ±15%) in diameter and the resolution of image sensor 614 may be known at the outset (e.g., settings) or may be determined (e.g., retrieved). In some aspects, computing system 602 may retrieve a configuration file associated with image sensor 614 to determine the resolution of image sensor 614. For example, computing system 602 may send an application programming interface (API) request (e.g., API call) to image sensor 614 to retrieve at least the resolution of image sensor 614 and a focal length of image sensor 614. Thus, a sufficiently accurate estimate of the z-dimension may be obtained using the size of the iris (nominal size) and the resolution of image sensor 614. For example, computing system 602 may determine the number of pixels across the iris diameter based on iris data 153. Computing system 602 may determine the z-dimension based on the number of pixels, the focal length, and the resolution of image sensor 614.

In some aspects, computing system 602 may employ artificial intelligence algorithms such as deep learning based methods (e.g., convolutional neural networks) to correct for motion blur in the eye image.

In 708, computing system 602 may locate the eyelids in each eye image by matching two quadratic functions to pixels having relatively high gradient suggesting an eyelid-pupil, eyelid-sclera, and/or eyelid-iris boundary. In some aspects, computing system 602 may determine a gradient vector at each pixel of the eye image. Then, computing system 602 may compute a gradient magnitude at each pixel from the gradient vector. The gradient magnitude may be compared with a threshold value. If the gradient magnitude exceeds the threshold value, then the respective pixel is matched with the two quadratic functions.

In 710, computing system 602 may locate a pupil and/or an iris in each eye image. Computing system 602 may implement eye segmentation techniques to locate the pupil and/or the iris. For example, eye segmentation techniques may include integro-differential operator, Hough transform, color component analysis, Zernike moments, or other techniques as described in *Handbook of Iris Recognition, 2nd edition*, Bowyer and Burge, editors, Springer-Verlag, London, 2016, Chapter 7: Methods of Iris Segmentation. In one example method, an ellipse is fitted to the dark to medium transition of the pupil-iris boundary, and a larger ellipse is fitted to the medium-to-bright transition of the iris-sclera boundary. In some aspects, a closed curve or contour may be fitted to the pupil-iris boundary and/or to iris-sclera boundary. For example, techniques such as geodesic active contours, variational level sets, or Fourier-based approximation may be implemented.

In 712, computing system 602 may calculate an iris rotation relative to the line of sight from image sensor 614 to the eye based on the time series of the shape of the best-fit iris-sclera ellipse or other contours.

In consumer electronic devices, the location and orientation of image sensor 614 is generally fixed relative to display device 616. In 714, computing system 602 may determine an iris rotation output. Computing system 602 may map the iris translation relative to image sensor 614 to a monitor-centered coordinate system (e.g., the monitor-centered 3D coordinate system of FIG. 3A) based on the fixed position of image sensor 614 relative to display device 616. More specifically, computing system 602 may map the iris rotation relative to the line of sight from image sensor 614 to the eye to be relative to the line of sight from the center of display device 616 (e.g., the origin of the monitor-centered 3D coordinate system of FIG. 3A) to the eye based on the fixed position of image sensor 614 relative to display device 616.

In 716, computing system 602 may map the time series of face locations relative to image sensor 614 to the monitored-center coordinate system (e.g., the monitor-centered 3D coordinate system of FIG. 3A) based on the fixed position of image sensor 614 relative to display device 616. Computing system 602 may also map the time series of face orientations relative to the line of sight from image sensor 614 to the eye be relative to the line of sight from the center of display device 616 (the origin of the monitor-centered 3D coordinate system of FIG. 3A) to the eye based on the fixed position of image sensor 614 relative to display device 616 to obtain a face orientation output.

In 718, computing system 602 may compare the iris rotation output from 714 to the face orientation output of 716 to get the iris rotation relative to the face-centered coordinate system (e.g., the face-centered coordinate system of FIG. 3B). Thus, the iris rotation relative to the skull of user 612 may be compared to results from other eye-tracking devices. For example, the iris rotation may be compared with results from a specialized or a high-precision near-infrared eye-tracker in a carefully controlled environment (e.g., absence of shadows from ambient light, little or no movement of the user, absence of glasses and makeup that may confuse the eye tracker).

In some aspects, 704-718 may be iteratively repeated to refine the accuracy. For example, 704-718 may be iteratively repeated to refine the accuracy compared to a specialized or a high-precision near-infrared eye-tracker in a carefully controlled environment. 704-718 may be repeated until a terminal condition is satisfied. The terminal condition may include a maximum number of iterations and/or an accuracy improvement or a desirable change in a value of one or more oculometric parameters between two consecutive iterations. For example, if a percentage change in the value of one or more oculometric parameters is less than a threshold, then the iterations are stopped.

Figure 8:
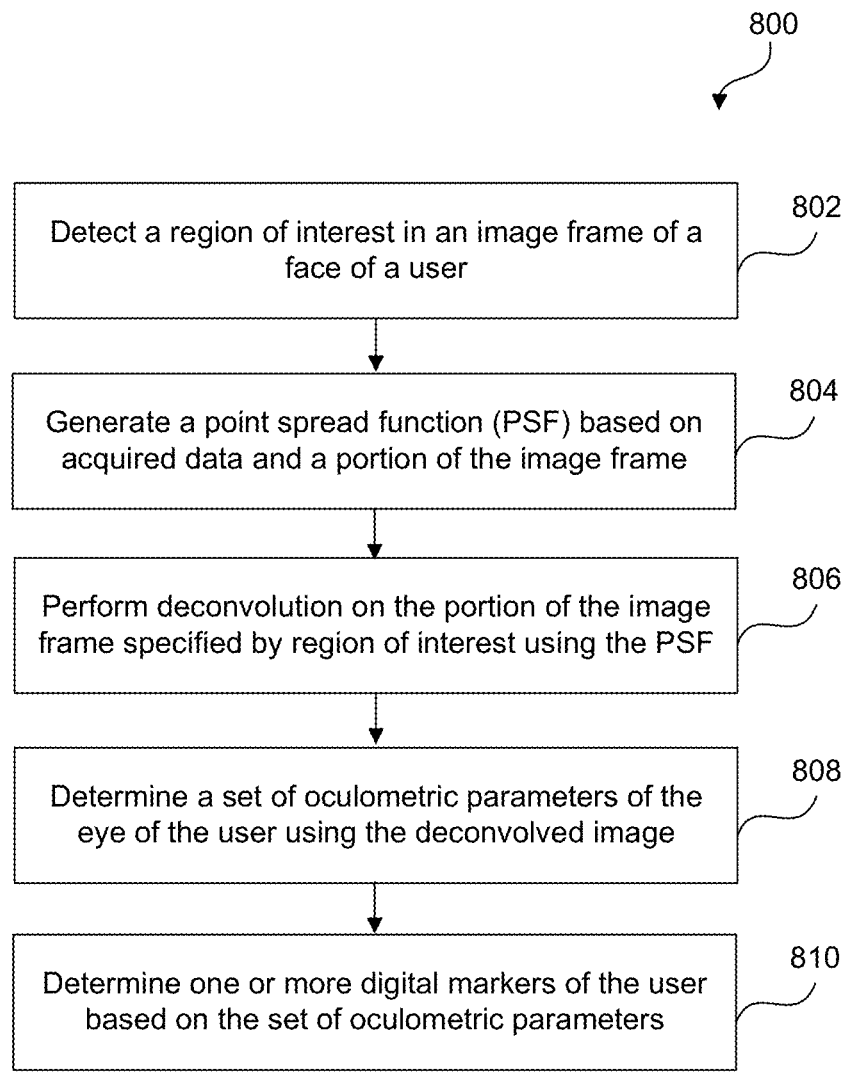
FIG. 8 is a flowchart for a method for determining one or more digital markers indicative of a neurological condition, according to some embodiments.

FIG. 8 is a flowchart for a method 800 for determining one or more digital markers indicative of a neurological condition, according to some embodiments. Method 800 can be performed by processing logic that can comprise hardware (e.g., circuitry, dedicated logic, programmable logic, microcode, and the like), software (e.g., instructions executing on a processing device), or a combination thereof. It is to be appreciated that not all steps may be needed to perform the disclosure provided herein. Further, some of the steps may be performed simultaneously, or in a different order than shown in FIG. 8, as will be understood by one of ordinary skill in the art.

Method 800 shall be described with reference to FIG. 6. However, method 800 is not limited to that example embodiment.

In 802, computing system 602 may detect a region of interest in an image frame of a face of user 604. The region of interest includes an eye of user 604 and the image frame may be obtained from a video stream.

In 804, computing system 602 may generate a PSF based on acquired data and a portion of the image frame specified by the region of interest. The acquired data may include the video data and the device data. The device data may include orientation information of the device. In some aspects, the PSF may include the effects of motion blur and/or inherent limitations of image sensor 614.

In some aspects, the acquired data may include a sclera brightness. A minimum sclera brightness threshold may be used to ensure sufficient signal-to-noise ratio to prevent the blind deconvolution from generating an unacceptable level of spurious artifacts.

In some aspects, computing system 602 may determine a pre-set of oculometric parameters based on the portion of the image frame. In some aspects, the PSF is further based on the pre-set of oculometric parameters.

In 806, computing system 602 may perform deconvolution on the portion of the image frame specified by the region of interest using the PSF.

In 808, computing system 602 may determine a set of oculometric parameters of the eye of the user using the deconvolved image. The oculometric parameters may include a pupil center, iris data, and eyelid data.

In some aspects, computing system 602 may detect a plurality of boundaries in the deconvolved image based on a change in intensity between data points in the deconvolved image. For example, computing system 602 may implement a gradient-based edge detection technique to detect the plurality of boundaries. Computing system 602 may implement a segmentation algorithm to identify different areas of the eye (e.g., iris, pupil, and/or eyelids). Then, computing system 602 may fit a plurality of quadratic curves to one or more of the identified areas (e.g., upper eyelid and/or lower eyelid). Computing system 602 may identify a quadratic curve from a plurality of quadratic curves. The identified quadratic curve fits the upper eyelid and the lower eyelid. In some aspects, the quadratic curve is identified based on the plurality of boundaries using a maximal likelihood estimation as described previously herein.

In 810, computing system 602 may determine one or more digital markers of user 604 based on the set of oculometric parameters. The one or more digital markers may be indicative of a neurological condition of user 604.

In some aspects, 804-810 may be iteratively repeated to improve the accuracy of the set of oculometric parameters compared to specialized or high precision near-infrared eye-trackers in a carefully controlled environment. In some aspects, 804-810 may be repeated until a terminal condition is satisfied and/or an accuracy improvement or a desirable change in a value of one or more oculometric parameters between two consecutive iterations. The terminal condition may include a maximal number of iterations. For example, a counter value may be incremented at each iteration and the counter value compared to the maximal number of iterations. Once the maximal number of iterations is reached, the iteration is stopped. In some aspects, the terminal condition may include determining an accuracy improvement percentage. For example, the improvement between two iterations (e.g., percentage) may be compared with the accuracy improvement percentage. If the improvement is less than the accuracy improvement percentage then the iterations are stopped. In some aspects, if the difference between digital markers of two consecutive iterations is less than a threshold, then the iterations are stopped.

Figure 9:
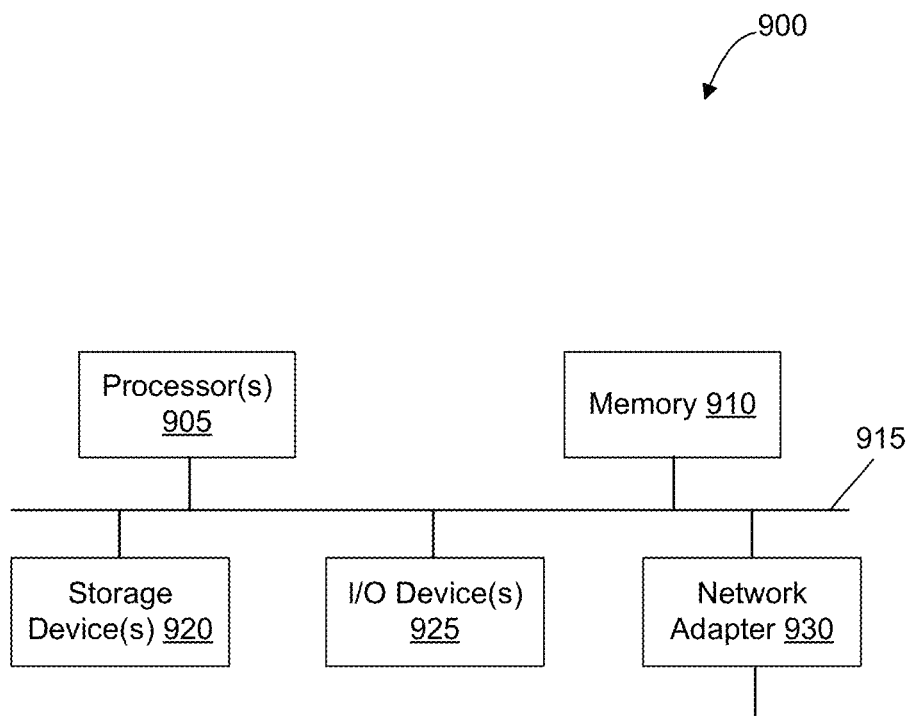
FIG. 9 is a block diagram of a computer system as may be used to implement features of the disclosed embodiments.

FIG. 9 is a block diagram of a computer system as may be used to implement features of the disclosed embodiments. The computer system 900 may be used to implement any of the entities, subsystems, components or services depicted in the examples of the foregoing figures (and any other components described in this specification). For example, the method steps of FIGS. 4, 5, 7, and 8 may be implemented via computer system 900. Computing system 602 may be implemented using combinations or sub-combinations of computer system 900. The computer system 900 may include one or more central processing units ("processors") 905, memory 910, input/output devices 925 (e.g., keyboard and pointing devices, display devices), storage devices 920 (e.g., disk drives), and network adapters 930 (e.g., network interfaces) that are connected to an interconnect 915. The interconnect 915 is illustrated as an abstraction that represents any one or more separate physical buses, point to point connections, or both connected by appropriate bridges, adapters, or controllers. The interconnect 615, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Components (IEEE) standard 1394 bus, also called "Firewire".

The memory 910 and storage devices 920 are computer-readable storage media that may store instructions that implement at least portions of the described embodiments. In addition, the data structures and message structures may be stored or transmitted via a data transmission medium, such as a signal on a communications link. Various communications links may be used, such as the Internet, a local area network, a wide area network, or a point-to-point dial-up connection. Thus, computer readable media can include computer-readable storage media (e.g., "non-transitory" media) and computer-readable transmission media. The storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The instructions stored in memory 910 can be implemented as software and/or firmware to program the processor(s) 905 to carry out actions described above. The processors may be programmed to execute computer program instructions by software; hardware; firmware; some combination of software, hardware, or firmware; and/or other mechanisms for configuring processing capabilities on the processors. In some aspects, such software or firmware may be initially provided to the computer system 900 by downloading it from a remote system through the computer system 900 (e.g., via network adapter 930).

The embodiments introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

Figure 10:
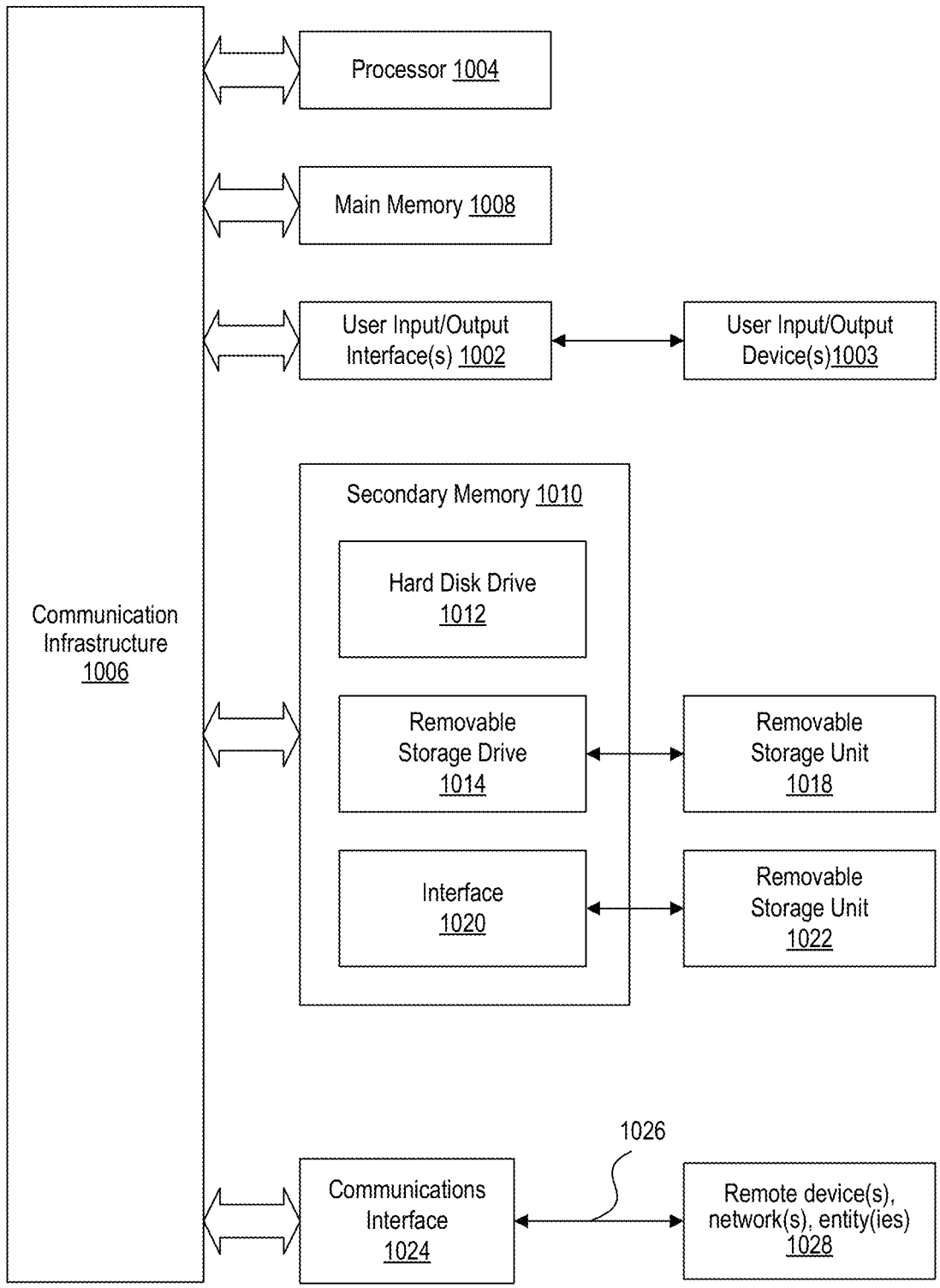
FIG. 10 shows a computer system for implementing various embodiments of this disclosure.

FIG. 10 shows a computer system 1000, according to some embodiments. Various embodiments and components therein can be implemented, for example, using computer system 1000 or any other well-known computer systems. For example, the method steps of FIGS. 7 and 8 may be implemented via computer system 1000.

In some aspects, computer system 1000 may comprise one or more processors (also called central processing units, or CPUs), such as a processor 1004. Processor 1004 may be connected to a communication infrastructure or bus 1006.

In some aspects, one or more processors 1004 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

In some aspects, computer system 1000 may further comprise user input/output device(s) 1003, such as monitors, keyboards, pointing devices, etc., that communicate with communication infrastructure 1006 through user input/output interface(s) 1002. Computer system 1000 may further comprise a main or primary memory 1008, such as random access memory (RAM). Main memory 1008 may comprise one or more levels of cache. Main memory 1008 has stored therein control logic (e.g., computer software) and/or data.

In some aspects, computer system 1000 may further comprise one or more secondary storage devices or memory 1010. Secondary memory 1010 may comprise, for example, a hard disk drive 1012 and/or a removable storage device or drive 1014. Removable storage drive 1014 may be a floppy disk drive, a magnetic tape drive, a compact disk drive, an optical storage device, tape backup device, and/or any other storage device/drive. Removable storage drive 1014 may interact with a removable storage unit 1018. Removable storage unit 1018 may comprise a computer usable or readable storage device having stored thereon computer software (control logic) and/or data. Removable storage unit 1018 may be a floppy disk, magnetic tape, compact disk, DVD, optical storage disk, and/any other computer data storage device. Removable storage drive 1014 reads from and/or writes to removable storage unit 1018 in a well-known manner.

In some aspects, secondary memory 1010 may comprise other means, instrumentalities or other approaches for allowing computer programs and/or other instructions and/or data to be accessed by computer system 1000. Such means, instrumentalities or other approaches may comprise, for example, a removable storage unit 1022 and an interface 1020. Examples of the removable storage unit 1022 and the interface 1020 may comprise a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

In some aspects, computer system 1000 may further comprise a communication or network interface 1024. Communication interface 1024 enables computer system 1000 to communicate and interact with any combination of remote devices, remote networks, remote entities, etc. (individually and collectively referenced by reference number 1028). For example, communication interface 1024 may allow computer system 1000 to communicate with remote devices 1028 over communications path 1026, which may be wired and/or wireless, and which may comprise any combination of LANs, WANs, the Internet, etc. Control logic and/or data may be transmitted to and from computer system 1000 via communications path 1026.

In some aspects, a non-transitory, tangible apparatus or article of manufacture comprising a non-transitory, tangible computer useable or readable medium having control logic (software) stored thereon is also referred to herein as a computer program product or program storage device. This includes, but is not limited to, computer system 1000, main memory 1008, secondary memory 1010, and removable storage units 1018 and 1022, as well as tangible articles of manufacture embodying any combination of the foregoing. Such control logic, when executed by one or more data processing devices (such as computer system 1000), causes such data processing devices to operate as described herein.

Based on the teachings contained in this disclosure, it will be apparent to those skilled in the relevant art(s) how to make and use embodiments of this disclosure using data processing devices, computer systems and/or computer architectures other than that shown in FIG. 10. In particular, embodiments may operate with software, hardware, and/or operating system implementations other than those described herein.

It is to be understood that the phraseology or terminology herein is for the purpose of description and not of limitation, such that the terminology or phraseology of the present disclosure is to be interpreted by those skilled in relevant art(s) in light of the teachings herein.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While specific embodiments of the disclosure have been described above, it will be appreciated that embodiments of the present disclosure may be practiced otherwise than as described. The descriptions are intended to be illustrative, not limiting. Thus, it will be apparent to one skilled in the art that modifications may be made to the disclosure as described without departing from the scope of the claims set out below.

The foregoing description of the specific embodiments will so fully reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein.

The breadth and scope of the protected subject matter should not be limited by any of the above-described exemplary embodiments, but should be defined only in accordance with the following claims and their equivalents.

What is claimed is:

1. A computer-implemented method for efficiently determining a digital marker indicative of a neurological condition or a mental health condition, comprising:
   detecting, using one or more processors, a region of interest in an image frame of a face of a user, wherein the region of interest includes an eye of the user and the image frame is obtained from a video stream;
   performing blind deconvolution on a portion of the image frame specified by the region of interest, wherein the portion of the image frame satisfies a signal to noise threshold;
   determining a set of oculometric parameters of the eye of the user using the blind deconvolved portion of the image frame; and
   determining one or more digital markers of the user based on the set of oculometric parameters, wherein the one or more digital markers are indicative of a neurological condition or a mental health condition of the user.

2. The computer-implemented method of claim 1, wherein the signal to noise threshold comprises a minimum sclera brightness.

3. The computer-implemented method of claim 1, wherein the oculometric parameters comprise a pupil center, iris data, and eyelid data.

4. The computer-implemented method of claim 1, wherein the performing blind deconvolution further comprises:
   determining a point spread function based on stimulus data or device data.

5. The computer-implemented method of claim 1, wherein the performing blind deconvolution further comprises:
   determining a spatial velocity based on a time series of a location of the eye of the user, wherein the time series is indicative of the location of the eye in a plurality of successive eye images obtained from the video stream; and determining a point spread function based on the spatial velocity.

6. The computer-implemented method of claim 1, further comprising:
adjusting a size of the region of interest to correct for a motion in a z-direction, wherein the z-direction corresponds to a direction perpendicular to an image sensor, and wherein the video stream is captured by the image sensor.

7. The computer-implemented method of claim 1, further comprising:
prior to the performing blind deconvolution on the portion of the image frame, determining a pre-set of oculometric parameters based on the portion of the image frame.

8. The computer-implemented method of claim 1, further comprising:
iteratively repeating the performing the blind deconvolution and the determining the set of oculometric parameters to improve an accuracy of the set of oculometric parameters.

9. The computer-implemented method of claim 1, wherein the determining the set of oculometric parameters comprises:
detecting a plurality of boundaries in the blind deconvolved portion of the image frame based on a change in intensity between data points in the blind deconvolved portion of the image; and
identifying, from a plurality of quadratic curves, a quadratic curve that fits an upper eyelid and a lower eyelid based on the plurality of boundaries.

10. The computer-implemented method of claim 9, wherein the identifying comprises:
identifying the quadratic curve based on a maximal likelihood estimation.

11. A system for efficiently determining a digital marker indicative of a neurological condition or a mental health condition, comprising:
one or more memories; and
at least one processor each coupled to at least one of the one or more memories and configured to perform operations comprising:
detecting a region of interest in an image frame of a face of a user, wherein the region of interest includes an eye of the user and the image frame is obtained from a video stream;
performing blind deconvolution on a portion of the image frame specified by the region of interest, wherein the portion of the image frame satisfies a signal to noise threshold;
determining a set of oculometric parameters of the eye of the user using the blind deconvolved portion of the image frame; and
determining one or more digital markers of the user based on the set of oculometric parameters, wherein the one or more digital markers are indicative of a neurological condition or a mental health condition of the user.

12. The system of claim 11, wherein the signal to noise threshold comprises a minimum sclera brightness.

13. The system of claim 11, wherein the oculometric parameters comprise a pupil center, iris data, and eyelid data.

14. The system of claim 11, wherein the performing blind deconvolution further comprises:

determining a spatial velocity based on a time series of a location of the eye of the user, wherein the time series is indicative of the location of the eye in a plurality of successive eye images obtained from the video stream; and determining a point spread function based on the spatial velocity.

15. The system of claim 11, wherein the operations further comprise:
adjusting a size of the region of interest to correct for a motion in a z-direction, wherein the z-direction corresponds to a direction perpendicular to an image sensor, and wherein the video stream is captured by the image sensor.

16. The system of claim 11, wherein the determining the set of oculometric parameters comprises:
detecting a plurality of boundaries in the blind deconvolved portion of the image frame based on a change in intensity between data points in the blind deconvolved portion of the image; and
identifying, from a plurality of quadratic curves, a quadratic curve that fits an upper eyelid and a lower eyelid based on the plurality of boundaries.

17. A non-transitory computer-readable medium having instructions stored thereon that, when executed by at least one computing device, cause the at least one computing device to perform operations comprising:
detecting a region of interest in an image frame of a face of a user, wherein the region of interest includes an eye of the user and the image frame is obtained from a video stream;
performing blind deconvolution on a portion of the image frame specified by the region of interest, wherein the portion of the image frame satisfies a signal to noise threshold;
determining a set of oculometric parameters of the eye of the user using the blind deconvolved portion of the image frame; and
determining one or more digital markers of the user based on the set of oculometric parameters, wherein the one or more digital markers are indicative of a neurological condition or a mental health condition of the user.

18. The non-transitory computer-readable medium of claim 17, wherein the signal to noise threshold comprises a minimum sclera brightness.

19. The non-transitory computer-readable medium of claim 17, wherein the performing blind deconvolution further comprises:
determining a spatial velocity based on a time series of a location of the eye of the user, wherein the time series is indicative of the location of the eye in a plurality of successive eye images obtained from the video stream; and
determining a point spread function based on the spatial velocity.

20. The non-transitory computer-readable medium of claim 17, the operations further comprising:
adjusting a size of the region of interest to correct for a motion in a z-direction, wherein the z-direction corresponds to a direction perpendicular to an image sensor, and wherein the video stream is captured by the image sensor.

* * * * *